United States Patent [19]

Girard et al.

[11] Patent Number: 4,761,425
[45] Date of Patent: * Aug. 2, 1988

[54] LEUKOTRIENE ANTAGONISTS

[75] Inventors: Yves Girard, Pierrsponds; Joshua Rokach, Laval, both of Canada

[73] Assignee: Merck Frosst Canada, Inc., Kirkland, Canada

[*] Notice: The portion of the term of this patent subsequent to Sep. 2, 2003 has been disclaimed.

[21] Appl. No.: 685,807

[22] Filed: Dec. 24, 1984

Related U.S. Application Data

[63] Continuation-in-part of Ser. No. 651,415, Dec. 27, 1983, abandoned.

[51] Int. Cl.[4] .................... A61K 31/35; C07D 311/24; C07D 311/22
[52] U.S. Cl. .................... 514/456; 549/401; 549/402
[58] Field of Search ................ 549/402, 401; 514/456

[56] References Cited

U.S. PATENT DOCUMENTS 4,609,744  9/1986  Young et al. .................... 549/409

FOREIGN PATENT DOCUMENTS 68739  1/1983  European Pat. Off. .

Primary Examiner—Nicky Chan
Attorney, Agent, or Firm—Gabriel Lopez; Hesna J. Pfeiffer

[57] ABSTRACT

Compounds having the formula:

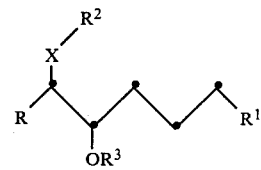

are antagonists of leukotrienes of $C_4$, $D_4$ and $E_4$, the slow reacting substance of anaphylaxis. These compounds are useful as anti-asthmatic, anti-allergic, anti-inflammatory agents, and cytoprotective agents.

8 Claims, No Drawings

LEUKOTRIENE ANTAGONISTS

This application is a continuation-in-part of U.S. Ser. No. 651,415, filed Dec. 27, 1983, abandoned.

This invention is directed to compounds which act as antagonists of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependert mechanism. Both groups of leukotrienes are formed following oxygenation of arachidonic acid through the action of a 5-lipoxygenase enzyme. See for example, D. M. Bailey et al., Ann. Rpts. Med. Chem. 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. Leukotriene antagonists or inhibitors would therefore be a new class of drugs for the treatment of asthma.

Psoriasis is a human skin disease which affects between two and six percent of the population. There is no adequate therapy for psoriasis and related skin conditions. The evidence for leukotriene involvement in these diseases is as follows. One of the earliest events in the development of preparpillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucociliary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function. See for example, B. Samuelsson, Science, 220 568 (1983).

Several classes of compounds exhibit ability to antagonize the action of leukotrienes in mammals, especially humans. See for example: United Kingdom Patent Specification Nos. 2,058,785 and 2,094,301; and European Patent Application Nos. 56,172, 61,800 and 68,739.

The present invention relates to compounds having activity as leukotriene and SRS-A antagonists or inhibitors, to methods for their preparation, to intermediates useful in their preparation and to methods and pharmaceutical formulations for using these compounds in mammals (especially humans). Because of their activity as leukotriene antagonists or inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure.

The compounds of this invention are best realized by Formula I:

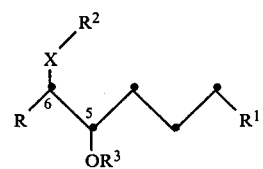

and pharmaceutically acceptable salts thereof, wherein;
X is O, S, SO, $SO_2$;
R is selected from: —CH=CH—($C_1$ to $C_{14}$ alkyl), —(CH=CH)$_2$—($C_1$ to $C_{12}$ alkyl), —(CH=CH)$_3$—($C_1$ to $C_{10}$ alkyl), —(CH=CH)$_3$—(CH$_2$—CH=CH)$_2$—($C_1$ to $C_4$ alkyl), —(CH=CH)$_4$—($C_1$ to $C_8$ alkyl), —CH$_2$—(CH=CH)$_4$—($C_1$ to $C_7$ alkyl), —(CH=CH)$_3$—CH$_2$CH=CH—(CH$_2$)$_n$CH$_2$OH wherein n is 1 to 6, —(CH=CH)$_3$—CH$_2$CH=CH—(CH$_2$)$_n$COOR$^{11}$ wherein n is 1 to 6, —(CH=CH)$_3$—CH$_2$CH=CH—($C_1$ to $C_7$ alkyl), —C≡C—($C_1$ to $C_{14}$ alkyl), —CH=CH—C≡C—($C_1$ to $C_{12}$ alkyl), —C≡C—(CH=CH)—($C_1$ to $C_{12}$ alkyl), —C≡C—(CH=CH)$_2$—($C_1$ to $C_{10}$ alkyl), and —C≡C—(CH=CH)$_2$—CH$_2$—CH=CH—($C_1$ to $C_7$ alkyl); COOR$^{11}$, CH$_2$OH, CHO, tetrazole, hydroxymethyl ketone, CN, CON(R$^4$)$_2$, CONHS$_2$R$^5$ a monocyclic or bicyclic heterocyclic ring containing an acidic hydroxyl group or HSO$_2$R$^5$; or

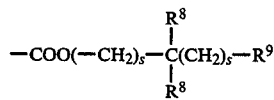

wherein each s is independently 0 to 3;
R$^9$ is
  (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
  (B) the radical wherein W-R$^{10}$ wherein W is O, S or NH and R$^{10}$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring;
each R$_8$ is independently H or alkyl of 1 to 4 carbons which may be straight chain or branched;
R$^2$ is

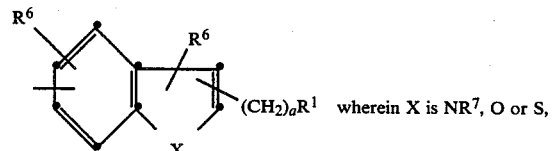

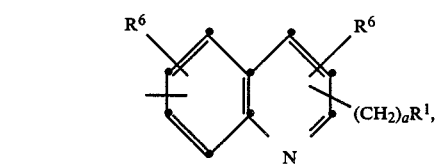

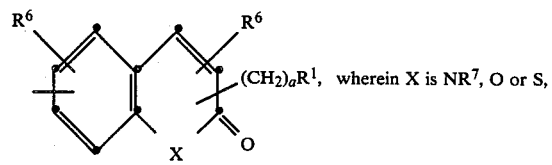

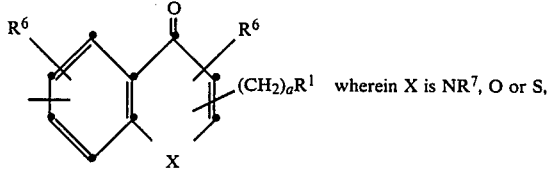

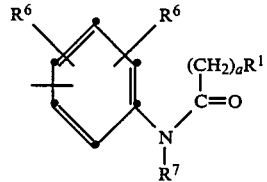

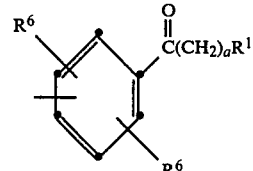

or

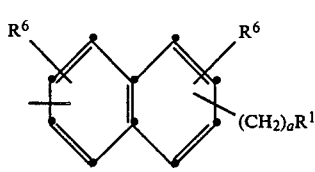

R$^3$ is H, lower alkyl, —(CH$_2$)$_a$COOR$^{11}$ or $C_1$ to $C_5$ acyl;
each R$^4$ is independently H, lower alkyl or two R$^4$ radicals may be joined to form a ring of from 5 to 8 members;
each R$^5$ is independently lower alkyl; CF$_3$; phenyl; or substituted phenyl, wherein the substituents are $C_1$ to $C_3$ alkyl, halogen, CN, CF$_3$, COOR$^4$ or $C_1$ to $C_3$ alkoxy;
each R$^6$ is independently H, lower alkyl, OH, halogen, $C_1$ to $C_3$ perfluoroalkyl, CN, NO$_2$, $C_1$ to $C_5$ acyl, COOR$^4$, SO$_2$N(R$^4$)$_2$, N(R$^4$)$_2$, OR$^5$, SR$^5$, SOR$^5$, SO$_2$R$^5$, O-aryl, benzyl, benzyl substituted as defined for phenyl in R$^5$, or CH$_2$OH;
each R$^7$ is independently H or R$^5$;
R$^{11}$ is H, lower alkyl, phenyl-lower alkyl, lower alkoxy-lower alkyl, lower acyloxy-lower alkyl; and
a is 0 to 4.

As used herein, the term "lower alkyl" includes those alkyl groups of from 1 to 7 carbon atoms of either a straight, branched or cyclic structure. Examples of lower alkyl fragments include methyl, ethyl, propyl, isopropyl, butyl sec- and tert-butyl, pentyl, hexyl, heptyl, cyclopropyl, cyclobutyl, cyclopentyl, cyclohexyl, cycloheptyl, and the like.

As used herein, the term alkyl includes lower alkyl and extends to cover carbon fragments having up to 20 carbon atoms in straight, branched or cyclic structures. Examples of alkyl groups include octyl, nonyl, undecyl, dodecyl, tridecyl, tetradecyl, pentadecyl, eicosyl, 3,7-ethyl-2,2-methyl-4-propylnonane and the like. The terms "lower alkyl" and "alkyl" also include groups having both straight chain and cyclic structures or both branched chain and cyclic structures.

As used herein, the term aryl includes the carbon containing aromatic structures such as phenyl, naphthyl, anthracentyl, phenanthrenyl, pyrenyl, phenyl substituted with one or more alkyls, naphthyl substituted with one or more alkyls, anthracenyl substituted with one or more alkyls, phenanthrenyl substituted with one as more alkyls, and the like.

As used herein, the term halogen refers to F, Cl, Br and I.

As used herein, heterocyclic rings include 5 or 6 membered rings containing one or more heteroatoms selected from O, N, S and bicyclic fused rings containing one or more heteroatoms selected from O, N or S. Generally useful heterocyclic rings include:

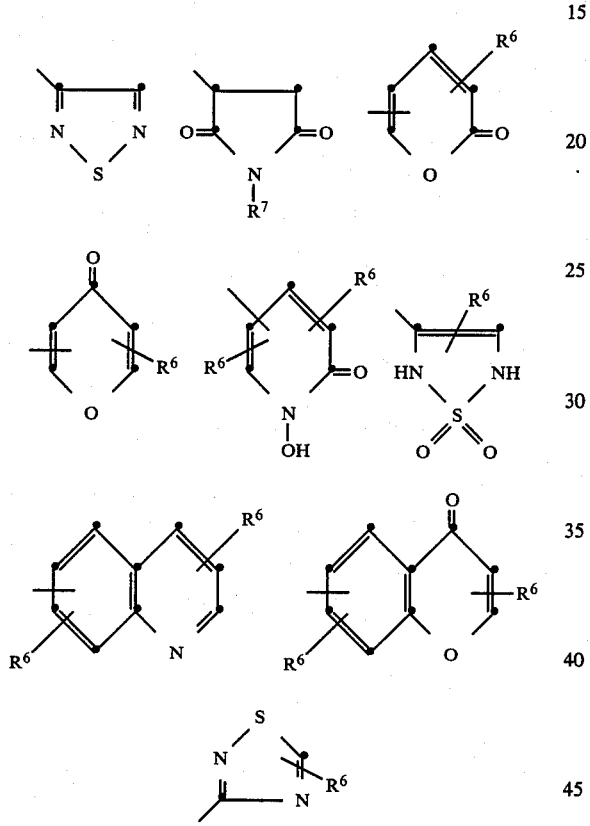

When R¹ is a carboxyl group in the Formula I compounds, they can also exist in a salt form. Furthermore, when R¹ is a carboxyl group or a derivative thereof and R³ is H, the compounds can also exist in a lactone form of Formula II. Both the salt and lactone forms of the Formula I compounds are embraced within the present invention.

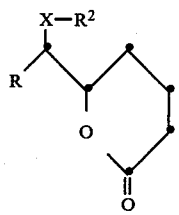

A preferred group of compounds is represented by Formula III:

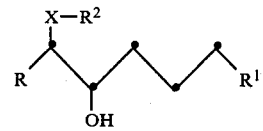

wherein:
x is O or S,
R is as defined for Formula I,
R¹ is COOR¹¹, CH₂OH, CHO or tetrazole,
R² is

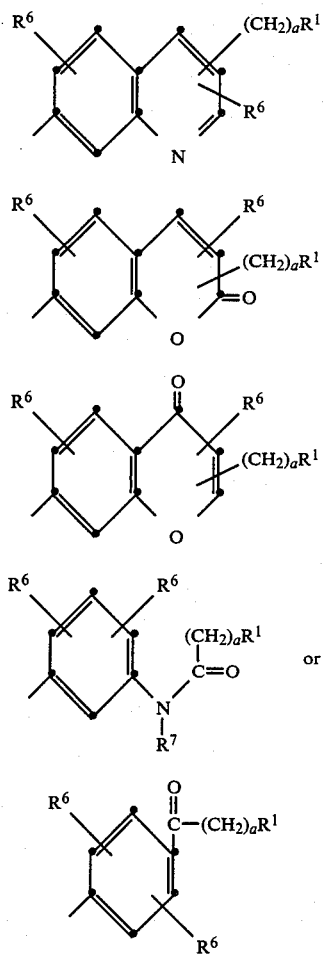

R⁶ is as defined for Formula I;
R¹¹ is as defined for Formula I; and
a is as defined for Formula I.

More preferred are the Formula III compounds wherein R¹ is or COOR¹¹ or CH₂OH.

The compounds of Formula I may be prepared by any process available to the skilled artisan. According to one method outlined in Scheme I racemic LTA₄ methyl ester, IV, (Rokach et al., *Tetrahedron Letters*, 21, 1485–1489 (1980)) is reacted with a suitable thiol in a solvent such as methanol, t-butanol and the like in the presence of a base such as a trialkylamine, to yield compound V (Cfr, Holme, et al., *Prostaglandins*, 20, 717–727 (1980)). The temperature of the reaction may be between −10° C. and 60° C., and it is conveniently carried out between 20° and 30° C. The reaction time may vary from 15 minutes to 6 hours, and the reaction progress may be followed by thin layer chromatography. Hydrolysis of the ester V is effected under the general conditions described by Rokach et al., *Tetrahedron Letters*, 21, 1485-1489 (1980), at temperatures ranging from −10° C. to 50° C. and preferably at as low a temperature as possible and which causes hydrolysis in a reasonable time, ranging from 1 hour to 5 days depending upon the particular compound. The salts are removed from the resulting solution of I by passage through a column of XAD resin, from which the product is obtained in the form of its potassium or sodium salt depending upon the base used for hydrolysis.

In this method the trans-LTA$_4$ methyl ester gives rise to the racemic erythro form of I and the cis isomer yields the racemic threo isomer of I.

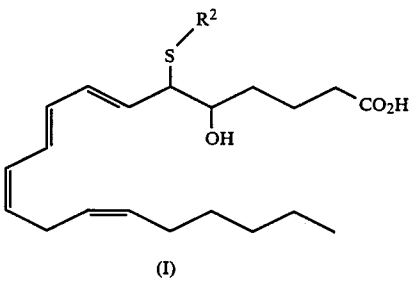

In Scheme II is illustrated a method of obtaining the optically active forms of compound I. In one method, compound VI (Rokach et al., *Tetrahedron Letters*, 22, 2759-2762 (1981)) is reacted with an alkylphosphonium salt, in the presence of an alkyl lithium to form an ylid species, in an unreactive solvent such as tetrahydrofuran at temperatures ranging from −78° C. to 25° C., preferably from −20° C. to 10° C., for from 30 minutes to 6 hours, depending upon the progress of the reaction which is followed by thin layer chromatography. Compound VII is converted to VIII and to I as in Scheme I.

In order to prepare the Formula I compounds with 2 or 3 double bonds, compound IX is prepared from VI according to the procedure of Rokach, et al., *Tetrahedron Letters*, 22, 979-982 (1981). Compound IX, where m is 1 or 2, is then converted to intermediates X and XI and finally hydrolyzed to I, as described previously.

By starting with any of the four possible optical isomers of VI, there can thus be obtained the four optically isomeric forms of the Formula I compounds.

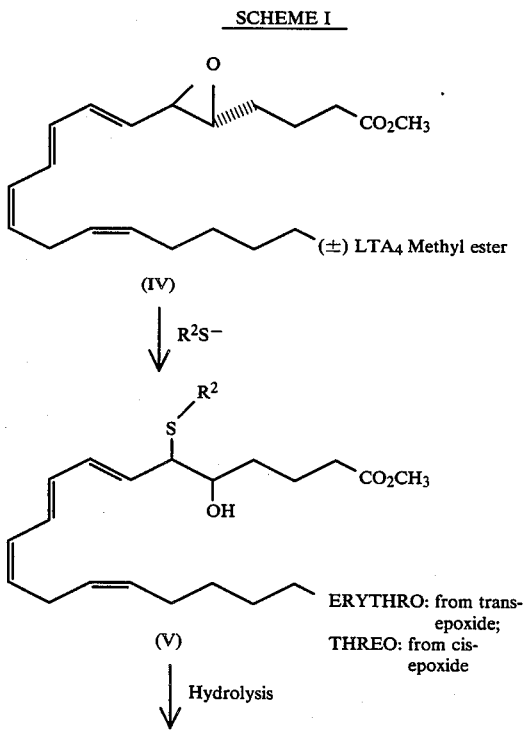

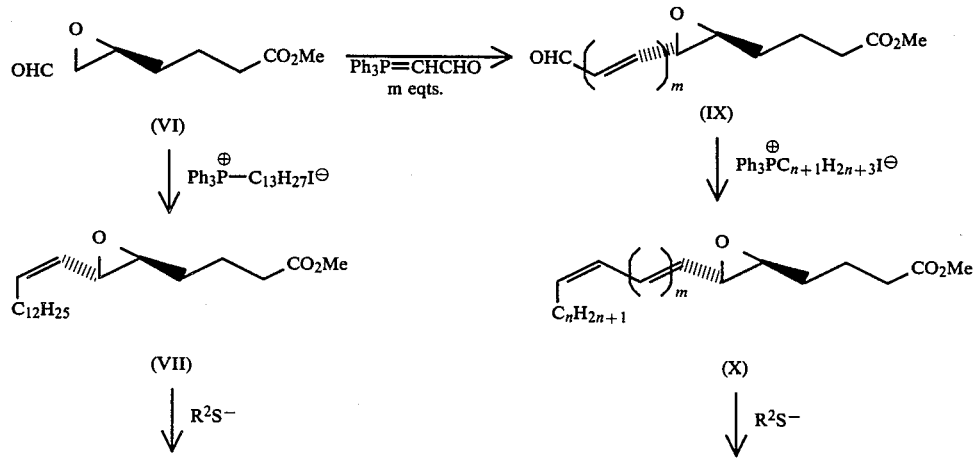

-continued
SCHEME II

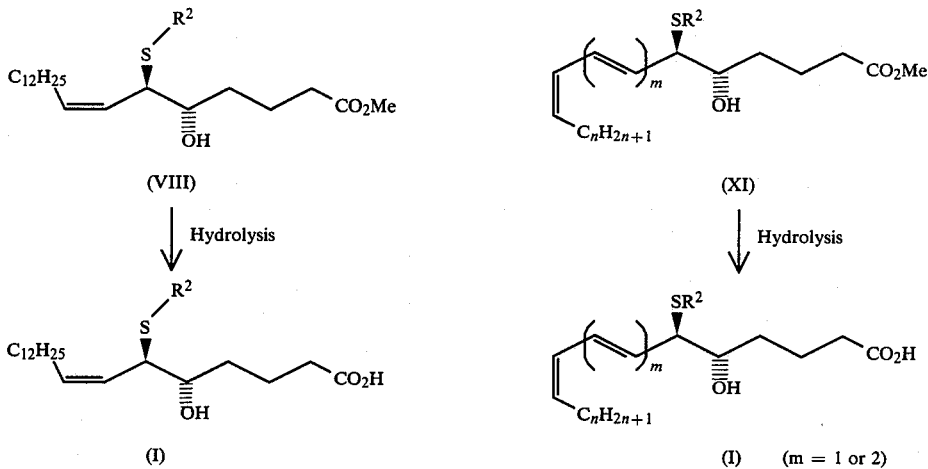

Pro-drug esters wherein $R^1$ is

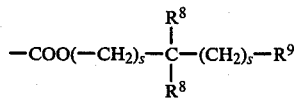

are obtained by reacting the sodium salt of Formula I ($R^1$=COONa) with

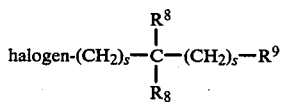

in an inert solvent such as DMF.

As will be appreciated, the compounds of Formula I possess chiral centers at $C_5$ and $C_6$ and, accordingly, exist in the stereoisomeric forms 5R, 6R; 5S, 6S; 5R, 6S and 5S, 6R. Other chiral centers are also possible, depending on the nature of the substituents R, $R^1$ and $R^2$, leading to further stereoisomeric forms. Further, where the compounds contain alkenyl substituents, for example as in R, cis-trans isomeric forms exist. It is not intended that the present invention be limited to any particular isomeric form.

A further embodiment of the present invention are pharmaceutical compositions comprising a compound of the Formula XII:

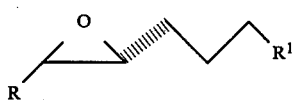

wherein R and $R^1$ are as defined for Formula I or a pharmaceutically acceptable salt thereof and the jagged bond indicates that both cis and trans isomers exist. Compounds of Formula XII are useful in inhibiting the biosynthesis of leukotrienes, and in particular the biosynthesis of leukotriene $B_4$ Particularly preferred compounds of Formula XII are those in which R does not contain three conjugated double bonds and in which $R^1$ is $COOR_8$ wherein $R^8$ is H or alkyl of 1 to 4 carbon atoms. Examples of such preferred compounds are the novel compounds of Formula XII identified below and in addition, the following two compounds: Methyl 5(S)-trans-5,6-oxido-7-(Z)-eicosenoate; Methyl 5(S)-trans-5,6-oxido-7(E),9(Z)-eicosadienoate;

When a salt form of compound XII is desired it is prepared by standard hydrolysis of XII ester. Typical conditions involve dissolving XII ester in methanol, adding 2N aqueous NaOH and stirring at room temperature for 2 hours to obtain a solution of XII salt.

The following compounds of the Formula XII are novel compounds:

(±)Methyl trans-5,6-oxidoeicos-7-ynoate;
Ethyl 5(S)-trans-5,6-oxidoeicos-7-ynoate;
Ethyl 5(S)-cis-5,6-oxidoeicos-7-ynoate;
Ethyl 5(S)-trans-5,6-oxidoeicos-9(E)-ene-7-ynoate;
(±)Methyl trans-5,6-oxidoeicosa-7(E), 9(E)-dienoate;
Ethyl 5(S)-trans-5,6-oxidoeicosa-7(E), 9(E)-dienoate;
Ethyl 5(S)-trans-5,6-oxidoeicosa-7(E), 9(E), 14(Z)-trienoate;
Sodium 5(S)-trans-5,6-oxidoeicos-7(E)-enoate;
Sodium 5(S)-trans-5,6-oxidoeicosa-7(E),9(Z)-dienoate;
(±)Sodium trans-5,6-oxidoeicos-7-ynoate;
Sodium 5(S)-trans-5,6-oxidoeicos-7-ynoate;
Sodium 5(S)-cis-5,6-oxidoeicos-7-ynoate;
Sodium 5(S)-trans-5,6-oxidoeicos-9(E)-ene-7-ynoate;
(±)Sodium trans-5,6-oxidoeicosa-7(E), 9(E)-dienoate.;
Sodium 5(S)-trans-5,6-oxidoeicosa-7(E), 9(E)-dienoate; and
Sodium 5(S)-trans-5,6-oxidoeicosa-7(E), 9(E), 14(Z)-trienoate.

The compounds of Formula I are active as antagonists of SRS-A and the leukotrienes $B_4$, $C_4$, $D_4$ and $E_4$. These compounds also have modest inhibitory activity on leukotriene biosynthesis but are primarily of therapeutic interest as antagonists. The compounds of the Formula XII are active as leukotriene inhibitors. The activity of the compounds of Formulae I and XII can be detected and evaluated by methods known in the art. See for example, Kadin, U.S. Pat. No. 4,296,129.

The ability of the compounds of Formula I to antagonize the effects of the leukotrienes and the ability of the compounds of the Formula XII to inhibit the leukotrienes makes them useful for inhibiting the symptoms induced by the leukotrienes in a human subject. The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. It will be understood that in this paragraph and in the discussion of methods of treatment which follows, references to the compounds of Formula I or XII are meant to include the pharmaceutically acceptable salts and lactone forms.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanolinduced lesion assay and (B) an indomethacin-induced ulcer assay.

A. Ethanol-Induced Gastric Ulcer Assay

Twenty-four hour fasted Sprague-Dawley (S.D.) rats are perorally (p.o.) dosed with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosae are examined for resulting lesions.

B. Indomethacin-Induced Ulcer Assay

Indomethacin, 10 mg/kg p.o., is used to induce ulcers in 24 hour fasted S.D. rats. Fifteen minutes prior to indomethacin administration, groups of rats each receive either an aqueous vehicle (5% by weight methylcellulose) or the test compound at various doses perorally. Four hours later the animals are sacrificed and stomach mucosae are examined for resulting ulcers.

The magnitude of a prophylactic or therapeutic dose of a compound of Formula I or XII will, of course, vary with the nature of the severity of the condition to be treated and with the particular compound of Formula I or XII and its route of administration. It will also vary according to the age, weight and response of the individual patient. In general, the daily dose range for anti-asthmatic, anti-allergic or anti-inflammatory use and generally, uses other than cytoprotection, lie within the range of from about 0.1 mg to about 40 mg per kg body weight of a mammal, preferably 0.2 mg to about 20 mg per kg, and most preferably 1 to 10 mg per kg, in single or divided doses. On the other hand, it may be necessary to use dosages outside these limits in some cases.

The exact amount of a compound of the Formula I or XII to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I or XII in avoiding future damage would be co-administration of a compound of the Formula I or XII with a non-steroidal antiinflammatory drug (NSAID) that might otherwise cause such damage (for example, indomethacin). For such use, the compound of Formula I or XII is administered from 30 minutes prior up to 30 minutes after administration of the NSAID. Preferably it is administered prior to or simultaneously with the NSAID, (for example, in a combination dosage form).

The effective daily dosage level for compounds of Formula I or XII inducing cytoprotection in mammals, especially humans, will generally range from about 0.02 mg/kg to about 40 mg/kg, preferably from about 0.2 mg/kg to about 20 mg/kg. The dosage may be administered in single or divided individual doses.

Any suitable route of administration may be employed for providing a mammal, especially a human with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

The pharmaceutical compositions of the present invention comprise a compound of Formula I or XII as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. The compositions include compositions suitable for oral, rectal, ophthalmic, pulmonary, nasal, dermal, topical or parenteral (including subcutaneous, intramuscular and intravenous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.1 mg to about 20 mg (preferably from about 0.1 mg to about 10 mg) of a compound of formula I per kg of body weight per day and for cytoprotective use from about 0.02 mg to about 40 mg (preferably from about 0.2 mg to about 20 mg and more preferably from about 1 mg to about 10 mg) of a compound of Formula I or XII per kg of body weight per day. In the case where an oral composition is employed, a suitable dosage range for anti-asthmatic, anti-inflammatory or anti-allergic use is, e.g. from about 1 mg to about 40 mg of a compound of formula I per kg of body weight per day, preferably from about 5 mg to about 20 mg per kg and for cytoprotective use from about 0.2 mg to about 40 mg (preferably from about 0.2 mg to about 20 mg and more preferably from about 0.2 mg to about 10 mg) of a compound of Formula I or XII per kg of body weight per day.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, the compounds of Formula I or XII can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to the common dosage forms set out above, the compounds of Formula I or XII may also be administered by controlled release means and/or delivery devices such as those described in U.S. Pat. Nos. 3,845,770; 3,916,899; 3,536,809; 3,598,123; 3,630,200 and 4,008,719, the disclosure of which is hereby incorporated herein by reference.

Pharmaceutical compositions of the present invention suitable for oral administration and by inhalation in the case of asthma therapy may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

The following are examples of representative pharmaceutical dosage forms for the compounds of

| Formula I or XII: | |
|---|---|
| Injectable Suspension | mg/ml |
| Compound of Formula I or XII | 2.0 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |
| Tablet | mg/tablet |
| Compound of Formula I or XII | 25.0 |
| Microcrystalline Cellulose | 325.0 |
| Providone | 14.0 |
| Microcrystalline Cellulose | 90.0 |
| Pregelatinized Starch | 43.5 |
| Magnesium Stearate | 2–2.5 |
| | 500 |
| Capsule | mg/capsule |
| Compound of Formula I or XII | 25.0 |
| Lactose Powder | 573.5 |
| Magnesium Stearate | 1.5 |
| | 600 |

In addition to the compounds of Formula I or XII, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I or XII to the second active ingredient may be varied and will depend upon the effective dose of each ingredient. Generally, an effective dose of each will be used. Thus, for example, when a compound of the Formula I or XII is combined with an NSAID the weight ratio of the compound of the Formula I or XII to the NSAID will generally range from about 200:1 to about 1:200. Combinations of a compound of the Formula I or XII and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

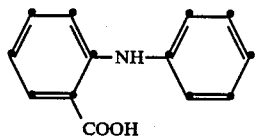

which can bear a variety of substituents and in which the free —COOH group can be in the form of a pharmaceutically acceptable salt group, e.g., —COO⁻Na⁺.

The biphenylcarboxylic acid derivatives which can be used comprise diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

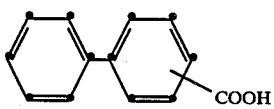

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4—(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula

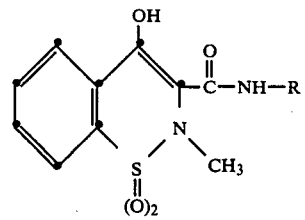

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used:
480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TVX2706, U60257, UR2301, and WY41770.

Finally, NSAIDs which may also be used include the salicylates, specifically aspirin, and the phenylbutazones, and pharmaceutically acceptable salts thereof.

Pharmaceutical compositions comprising the Formula I or XII compounds may also contain inhibitors of the biosynthesis of the leukotrienes such as are disclosed in pending U.S. patent application Ser. Nos. 539,342, filed Oct. 5, 1983, 459,924, filed Jan. 21, 1983, 539,215, filed Oct. 5, 1983, and 547,161, filed Oct. 31, 1983, which are hereby incorporated herein by reference.

The compounds of the Formula I or XII may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European patent application Nos. 56,172 and 61,800; and in U.K. patent specification No. 2,058,785, which are hereby incorporated herein by reference.

Pharmaceutical compositions comprising the Formula I or XII compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I or XII may also be advantageously combined with an $H_1$ or $H_2$-receptor antagonist, such as for instance cimetidine, ranitidine, terfenadine, famotidine, aminothiadiazoles disclosed in EP No. 40,696 and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The following examples are provided to aid in the interpretation of the present invention. They are not intended to limit the scope of the invention in any manner. Infrared (IR) spectra were measured as KBr disks or as thin films and absorption bands are reported in reciprocal centimeters ($cm^{-1}$). Nuclear magnetic resonance (NMR) spectra (90 MHz) were measured in deuterochloroform ($CDCl_3$), perdeuterodimethyl sulfoxide (DMSO-$d_6$), perdeuteromethanol ($CD_3OD$), deuterium oxide ($D_2O$) or deuterated trifluoroacetic acid ($CF_3COOD$) and peak positions are expressed in parts per million (ppm) downfield from an internal reference, tetramethylsilane. The following abbreviations are used for peak shapes: s, singlet; d, doublet; t, triplet; q, quartet; and m, multiplet. All melting and boiling points are reported in degrees Centigrade (°C.) and are uncorrected.

EXAMPLE 1

Preparation of 7-mercapto-8n-propyl-4-oxo-4H-1-benzopyran-2-carboxylic acid and methyl ester

Step 1

O-[(2-Carbethoxy-8n-propyl-4-oxo-4H-1-benzopyran)-7-yl]dimethylcarbamothioate

2-Carbethoxy-7-hydroxy-8-n-propyl-4-oxo-4H-1-benzopyran (1 g) in anhydrous DMF (4 ml) was cooled to 0° and treated under $N_2$ with sodium hydride (50% dispersion in mineral oil, 180 mg) with stirring for 30 minutes. Dimethylcarbamothioic acid chloride (465 mg) was added and the mixture was stirred 15 minutes at 0°, warmed to 80° and maintained for 18 hours. The mixture was cooled, diluted with $CH_2Cl_2$ (50 ml) and washed with water (3×100 ml), dried over $Na_2SO_4$ and reduced to dryness in vacuo. The residue was crystallized from ethyl acetate and hexane to yield the title compound, m.p. 132°-134°.

Analysis, calculated: C, 59.50; H, 5.82; N, 3.85; S, 8.82. Observed: C, 59.60; H, 5.47; N, 3.73; S, 8.56.

Step 2

S-[(2-Carbethoxy-8n-propyl-4-oxo-4H-1-benzopyran)-7-yl]dimethylcarbamothioate

The ester prepared in Step 1 (1 g) was heated neat under a nitrogen atmosphere to 200° for 2 hours. After cooling the residue was crystallized from ethyl acetate and hexane to yield the title compound, m.p. 113°-114°.

Analysis, calculated: C, 59.50; H, 5.82; N, 3.85; S, 8.82. Observed: C, 59.49; H, 5.94; N, 3.86; S, 9.10.

Step 3

2-Carboxy-7-mercapto-8n-propyl-4-oxo-4H-1-benzopyran

Sodium (69.0 mg) was dissolved in anhydrous methanol (50 ml) and to this was added the ester (1 g) from Step 2. The mixture was stirred under a nitrogen atmosphere for 3 hours at ambient temperature. Water (50 ml) was added and the mixture was acidified with 6N HCl. The resulting crystals were collected by filtration and recrystallized from ethyl acetate to provide the title compound m.p. 206°-208°.

Analysis, calculated: C, 59.08; H, 4.58; S, 12.13. Observed: C, 59.50; H, 4.55; S, 11.92.

Step 4

3-Carbomethoxy-7-mercapto-8n-propyl-4-oxo-4H-1-benzopyran

The acid from Step 3 (6.6 g) was dissolved in a mixture of hydrogen chloride (18 g) and anhydrous methanol (200 ml). The mixture was stirred overnight under a $N_2$ atmosphere at ambient temperature. The mixture was reduced to dryness in vacuo to provide the title compound, m.p. 98°-99°.

EXAMPLE 2

Preparation of 2-carbomethoxy-7-mercapto-4-oxo-4H-1-benzopyran and 2-hydroxymethyl-7-mercapto-4-oxo-4H-1-benzopyran

Step 1

O-[(2-Carbethoxy-4-oxo-4H-1-benzopyran)-7-yl]dimethylcarbamothioate

Following the procedure of Step 1, Example 1 but substituting an equivalent amount of 2-carbethoxy-7-hydroxy-4-oxo-4H-1-benzopyran for 2-carbethoxy-7-hydroxy-8-n-propyl-4-oxo-4H-1-benzopyran, there was obtained the title compound, m.p. 160°-161°.

Step 2

S-[(2-Carbethoxy-4-oxo-4H-1-benzopyran)-7-yl]dimethylcarbamothioate

Following the procedure of Step 2 of Example 1 but substituting the ester from Step 1 above for O-[(2-carbethoxy-8n-propyl-4-oxo-4H-1-benzopyran)-7-yl]dimethylcarbamothioate, there was obtained the title compound, m.p. 142°-143°.

Analysis, calculated: C, 56.07; H, 4.70; S, 9.98. Observed: C, 55.95, H, 4.70; S, 9.98.

Step 3

2-Carboxy-7-mercapto-4-oxo-4H-1-benzopyran

Following the procedure of Step 3 of Example 1 but substituting an equivalent amount of the ester of Step 2 above for S-[(2-carbethoxy-8n-propyl-4-oxo-4H-1-benzopyran)-7-yl]dimethylcarbamothioate, there was obtained the title compound, m.p. 261° (decomposition).

Step 4

2-Carbomethoxy-7-mercapto-4-oxo-4H-1-benzopyran

Following the procedure of Step 4 of Example 1 but substituting an equivalent amount of the acid from Step 3 above for 2-carboxy-7-mercapto-8n-propyl-4-oxo-4H-1-benzopyran, there was obtained the title compound, m.p. 147°-150°.

Analysis, calculated: C, 55.93; H, 3.41; S, 13.57. Observed: C, 55.53; H, 3.40; S, 13.69.

Step 5

2-Hydroxymethyl-7-mercapto-4-oxo-4H-1-benzopyran

The ester from Step 4 (3.0 g) in suspension in methanol (20 ml) and water (40 ml) at 0° was stirred vigorously during the portionwise addition of $NaBH_4$ (1.8 g). The mixture was stirred for 2 hours at 5°. Acetone (1 ml) was added followed by acidification with 1N HCl and extraction with methanolchloroform (1:9, 3×50 ml). The combined extracts were dried ($Na_2SO_4$), reduced to dryness in vacuo and the residue was recrystallized from methanolethyl acetate to provide the title compound, m.p. 139°-140°.

Analysis, calculated: C, 57.68; H, 3.87, S, 15.40. Observed: C, 58.10; H, 3.73; S, 15.53.

EXAMPLE 3

Preparation of 5,6-erythro-5-hydroxy-6-(2-carboxy-8n-propyl-4-oxo-4H-1-benzopyran-7-yl)thio-7,9-trans-11,14-cis-eicosatetraenoic acid

Step 1

Methyl 5,6-erythro-5-hydroxy-6-(2-carbo methoxy-8-propyl-4-oxo-4H-1-benzopyran-7-yl)-thio-7,9-trans-11,14-cis-eicosatetraenoate Methyl 7-mercapto-8n-propyl-4-oxo-4H-1-benzopyran-2-carboxylate (from Example 1) (60 mg) was added under nitrogen to methyl trans-5,6-oxido-7,9-trans-11,14-cis-eicosatetraenoate (60 mg) followed by a (2:1) mixture of methanol:triethylamine (0.3 ml) and the resulting mixture was stirred 1 hour at room temperature. After evaporation, the resulting oily residue was chromatographed on a silica gel column eluting with 40% ethyl acetate in heptane to afford the title compound; NMR ($CD_3OD$)$\delta$: 0.8-2.2 (m, 22H, —($C_2H_4$—, —$C_3H_7$, —$C_5H_{11}$), 2.3 (t, 2H, $CH_2CO_2CH_3$), 2.85 (dd, 2$H_{13}$), 3.65 (s, 3H, $CH_2CO_2CH_3$), 3.7-4.1 (m, 2H $H_5$, $H_6$), 4.0 (s, 3H, $CO_2CH_3$), 5.2-6.6 (m, 8H, olefins), 7.0 (s, 1H, $H_3$ (ar)), 7.55 (d, 1H $H_6$(ar), $J_{6,5}$=9 Hz) and 7.90 (d, 1H, $H_5$ (ar) $J_{5,6}$=9 Hz); UV spectrum, $\lambda_{MeOH}^{max}$ 268 nm (50,000).

Step 2

5,6-Erythro-5-hydroxy-6-(2-carboxy-8n-propyl-4-oxo-4H-1-benzopyran-7-yl)thio-7,9-trans-11,14-cis-eicosatetraenoic acid The diester prepared in Step 1 was stirred in a (1:1) mixture methanol and 1M $K_2CO_3$ for 3 days at 5° C. The hydrolysis was followed by reversed phase HPLC eluting with $CH_3CN:H_2O:AcOH$ (40:60:0.1) buffered with $NH_4OH$ to pH 5.6. The hydrolysis mixture was desalted on an XAD-8 resin column to provide the potassium salt of the title compound; U.V. spectrum, $\lambda_{MeOH}^{max}$ 271 nm (50,000).

EXAMPLE 4

Preparation of 5,6-threo-5-hydroxy-6-(2-carboxy-8n-propyl-4-oxo-4H-1-benzopyran-7-yl)thio-7,9-trans-11,14-cis-eicosatetraenoic acid

Step 1

Methyl 5,6-threo-5-hydroxy-6-(2-carbo methoxy-8n-propyl-4-oxo-4H-1-benzopyran-7 yl)thio-7,9-trans-11,14-cis-eicosatetraenoate Following the procedure of Step 1 of Example 3 but substituting an equivalent amount of methyl cis-5,6-oxido-7,9-trans-11,14-cis-eicosatetraenoate for methyl trans-5,6-oxido-7,9-trans-11,14-cis-eicosatetraenoate there was obtained the title compound; U.V. spectrum, $\lambda_{MeOH}^{max}$ 269 nm (50,000).

Step 2

5,6-Threo-5-hydroxy-6-(2-carboxy-8n-propyl-4-oxo-4H-1-benzopyran-7-yl)thio-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, there was obtained the title compound; U.V. spectrum, $\lambda_{MeOH}^{max}$ 272 nm (50,000).

EXAMPLE 5

Preparation of 5,6-erythro-5-hydroxy-6-(2-carboxy-4-oxo-4H-1-benzopyran-7-yl)thio-7,9-trans-11,14-cis-eicosatetraenoic acid

Step 1

Methyl 5,6-erythro-5-hydroxy-6-(2-carbomethoxy-4-oxo-4H-1-benzopuran-7-yl)thio-7,9-trans-11,14-cis-eicosatetraenoate Following the procedure of Step 1 of Example 3 but substituting an equivalent amount of methyl 7-mercapto-4-oxo-4H-1-benzopyran-2-carboxylate (from Example 2) for methyl 7-mercapto-8n-propyl-4-oxo-4-H-1-benzopyran-2-carboxylate there was obtained the title compound; U.V. spectrum, $\lambda_{MeOH}^{max}$ 268 nm (50,000), 280 nm (sh).

Step 2

5,6-Erythro-5-hydroxy-6-(2-carboxy-4-oxo-4-H-1-benzopyran-7-yl)thio-7,9-trans-11,14-cis-cicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate acid, there was obtained the title compound; U.V. spectrum, $\lambda_{MeOH}^{max}$ 268 nm (50,000), 280 nm (45,000).

EXAMPLE 6

Preparation of 5,6-threo-5-hydroxy-6-(2-carboxy-4-oxo-4H-1-benzopyran-7-yl)thio-7,9-trans-11,14-cis-eicosatetraenoic acid

Step 1

Methyl 5,6-threo-5-hydroxy-6-(2-carbomethoxy-4-oxo-4H-1-benzopyran-7-yl)thio-7,9-trans-11,14-cis-eicosatetraenoate Following the procedure of Step 1 of Example 3 but substituting an equivalent amount of methyl cis-5,6-oxido-7,9-trans-11,14-cis-eicosatetraenoate for methyl trans-5,6-oxido-7,9-trans-11,14-cis-eicosatetraenoate and substituting methyl 7-mercapto-4-oxo-4H-1-benzopyran-2-carboxylate for methyl 7-mercapto-8n-propyl-4-oxo-4H-1-benzopyran-2-carboxylate, there was obtained the title compound; U.V. spectrum, $\lambda_{MeOH}^{max}$ 268 nm (50,000), 280 nm (sh).

Step 2

5,6-Threo-5-hydroxy-6-(2-carboxy-4-oxo-4H-1-benzopyran-7-yl)thio-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, there was obtained the title compound; U.V. spectrum, $\lambda_{MeOH}^{max}$ 267 nm (50,000), 280 nm (45,000).

EXAMPLE 7

Preparation of 5,6-erythro-5-hydroxy-6-(2-hydroxymethyl-4-oxo-4H-1-benzopyran-7-yl)thio-7,9-trans-11,14-cis-eicosatetraenoic acid

Step 1

Methyl 5,6-erythro-5-hydroxy-6-(2-hydroxymethyl-4-oxo-4H-1-benzopyran-7-yl)thio-7,9-trans-11,14-cis-eicosatetraenoate Following the procedure of Step 1 of Example 3 but substituting an equivalent amount of 7-mercapto-2-hydroxymethyl-4-oxo-4H-1-benzopyran (from Example 2) for methyl 7-mercapto-8n-propyl-4-oxo-4H-1-benzopyran-2-carboxylate, there was obtained, after chromatography on a silica gel column eluting with a 10:10:1) mixture of heptane:EtOAc:MeOH, the title compound. NMR (CD$_3$OD) δ: 0.8–2.2 (m, 15H, —C$_2$H$_4$—, C$_5$H$_{11}$), 2.4 (t, 2H, CH$_2$CO$_2$CH$_3$), 2.93 (t, 2H, H$_{13}$), 3.67 (S, 3H, CO$_2$CH$_3$), 3.9 m, 1H, H$_5$), 4.1 (dd, 1H, H$_6$), 4.5 (s, 2H, CH$_2$OH), 5.2–6.5 (m, 9H, olefins H$_3$ (ar)), 7.4 (dd, 1H, H$_6$(ar), J$_{6,5}$=9 Hz, J$_{6,8}$=2 Hz), 7.47 (d, 1H, H$_8$(ar), J$_{8,6}$=2 Hz) and 8.0 (d, 1H, H$_5$(ar), J$_{5,6}$=9 Hz); U.V. spectrum, $\lambda_{MeOH}^{max}$ 280 nm (56,700).

Step 2

5,6-Erythro-5-hydroxy-6-(2-hydroxymethyl-4-oxo-4H-1-benzopyran-7-yl)thio-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, there was obtained the title compound; U.V. spectrum, $\lambda_{MeOH}^{max}$ 280 nm (56,700).

EXAMPLE 8

Preparation of 5,6-threo-5-hydroxy-6-(2-hydroxymethyl-4-oxo-4H-1-benzopyran-7-yl)thio-7,9-trans-11,14-cis-eicosatetraenoic acid

Step 1

Methyl 5,6-threo-5-hydroxy-6-(2-hydroxymethyl-4-oxo-4H-1-benzopyran-7-yl)thio-7,9-trans-11,14-cis-eicosatetraenoate Following the procedure of Step 1 of Example 3 but substituting an equivalent amount of methyl cis-5,6-oxido-7,9-trans-11,14-cis-eicosatetraenoate for methyl trans-5,6-oxido-7,9-trans-11,14-cis-eicosatetraenoate and substituting 7-mercapto-2-hydroxymethyl-4-oxo-4H-1-benzopyran (from Example 2) for methyl 7-mercapto-8n-propyl-4-oxo-4H-1-benzopyran-2-carboxylate there was obtained, after chromatography on a silica gel column eluting with a (10:10:1) mixture of heptane:EtOAc:MeOH, the title compound. NMR (CD$_3$OD): 0.8–2.2 (m, 15H, —C$_2$H$_4$—C$_5$H$_{11}$), 2.4 (t, 2H, CH$_2$CO$_2$CH$_3$), 3.96 (t, 2H, H$_{13}$), 3.7 (s, 3H, CO$_2$CH$_3$), 3.83 (m, 1H, H$_5$), 4.1 (dd, 1H, H$_6$), 4.52 (s, 2H, CH$_2$OH), 5.2–6.5 (m, 9H, olefins, H$_3$ (ar)), 7.47 (dd, 1H, H$_6$ (ar) J$_{6,5}$=9 Hz, J$_{6,8}$=2 Hz), 7.55 (d, 1H, H$_8$ (ar), J$_{8,6}$=2 Hz) and 8.07 (d, 1H, H$_5$ (ar), J$_{5,6}$=9 Hz); U.V. spectrum, $\lambda_{MeOH}^{max}$ 280 nm (56,700).

Step 2

5,6-Threo-5-hydroxy-6-(2-hydroxymethyl-4-oxo-4H-1-benzopyran-7-yl)thio-7,9-trans-11,4-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate there was obtained the title compound; U.V. spectrum, $\lambda_{MeOH}^{max}$ 280 nm (56,700).

EXAMPLE 9

Preparation of 5,6-erythro-5-hydroxy-6-(2-carboxy-4-oxo-4H-1-benzopyran-7-yl)oxo-7,9-trans-11,14-cis-eicosatetraenoic acid

Step 1

Methyl 5,6-erythro-5-hydroxy-6-(2-carbethoxy-4-oxo-4H-1-benzopyran-7-yl)oxo-7,9-trans-11,14-cis-eicosatetraeoate A solution of ethyl 7-trimethylsilyloxy-4-oxo-4H-1-benzopyran-2-carboxylate (200 mg) in CH$_2$Cl$_2$ (2.0 ml) was added to methyl trans-5,6-oxido-7,9-trans-11,14-cis-eicosatetraenoate (50 mg) followed by the addition of methanol (0.02 ml) and the reaction mixture was stirred at room temperature overnight. After evaporation, the resulting oily residue was chromatographed on a silica gel column eluting with a (10:10:0.5) mixture of heptane:EtOAc: (C$_2$H$_5$)$_3$N to provide the title compound. NMR (CD$_3$OD) δ: 0.7–2.2 (m, H$_{18}$, —C$_2$H$_4$—, C$_5$H$_{11}$, CO$_2$CH$_2$CH$_3$), 2.4 (t, 2H, CH$_2$CO$_2$CH$_3$), 2.92 (t, 2H, H$_{13}$), 3.67 (s, 3H, CO$_2$CH$_3$), 3.82 (m, 1H, H$_5$), 4.43 (quartet, 2H, CO$_2$CH$_2$CH$_3$), 4.80 (m, 1H, H$_6$), 5.2–6.8 (m, 8H, olefins), 6.92 (s, 1H, H$_3$ (ar)) 7.08 (d, 1H, H$_8$(ar), $J_{8,6}=2$ Hz), 7.12 (dd, 1H, H$_6$ (ar), $J_{6,5}=9$ Hz, $J_{6,8}=2$ Hz) and 7.98 (d, 1H, H$_5$ (ar), $J_{5,6}=9$ Hz); U.V. spectrum, $\lambda_{MeOH}{}^{max}$ 276 nm (46,600).

Step 2

5,6-Erythro-5-hydroxy-6-(2-carboxy-4-oxo-4H-1-benzopyrano-7-yl)oxo-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraneoate, there was obtained the title compound, U.V. spectrum, $\lambda_{MeOH}{}^{max}$ 276 nm (46,600).

EXAMPLE 10

Preparation of 5,6-erythro-5-hydroxy-6-(2-carboxy-8n-propyl-4-oxo-4H-1-benzopyran-7-yl)thio-7,9,11-trans-14-cis-eicosatetraenoic acid Step 1

Methyl 5,6-erythro-5-hydroxy-6-(2-carbomethoxy-8n-propyl-4-oxo-4H-1-benzopyran-7-yl)thio-7,9,11-trans-14-cis-eicosatetraenoate Following the procedure of Step 1 of Example 3 but substituting methyl trans-5,6-oxido-7,9,11-trans-14-cis-eicosatetraenoate (see: S. W. McKay et al., *J. Chromatog.* 214 249–256 (1981)) for methyl trans-5,6-oxido-7,9-trans-11,14-cis-eicosatetraenoate, the title compound is obtained.

Step 2

5,6-Erythro-5-hydroxy-6-(2-carboxy-8-n-propyl-4-oxo-4H-1-benzopyran-7-yl)thio-7,9,11-trans-14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 11

Preparation of 5,6-erythro-5-hydroxy-6-(2-carboxy-8n-propyl-4-oxo-4H-1-benzopyran-7-yl)thio-7,9-trans-11-cis-eicosatrienoic acid Step 1

Methyl 5,6-erythro-5-hydroxy-6-(2-carbomethoxy-8-n-propyl-4-oxo-4H-1-benzo-pyran-7-yl)thio-7,9-trans-11-cis-eicosatrienoate Following the procedure of Step 1 of Example 3 but substituting methyl trans-5,6-oxido-7,9-trans-11-cis-eicosatrienoate (see S. W. McKay et al., *J. Chromatog.* 214 249–256 (1981)) for methyl trans-5,6-oxido-7,9-trans-11,14-cis-eicosatetraenoate, the title compound is obtained.

Step 2

5,6-Erythro-5-hydroxy-6-(2-carboxy-8n-propyl-4-oxo-4H-1-benzopyran-7-yl)thio-7,9-trans-11-cis-eicosatrienoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 12

Preparation of 5(S)-hydroxy-6(R)-(2-carboxy-4-oxo-4H-1-benzopyran-7-yl)thio-7-cis-eicosenoic acid Step 1

Methyl 5(S),6(S)-oxido-7-cis-eicosenoate

A solution of n-BuLi in hexane (0.79 ml, 1.26 mmol) was added to a solution of triphenyl tridecanyl phosphonium iodide (1.17 g, 2 mmol) in THF (5 ml) at 0° C. and stirred for 5 minutes. To this solution was added a solution of methyl 6-formyl- 5(S),6(S)-oxido-hexanoate (see, J. Rokach et al., *Tet. Lett.*, 22 2759–2762 (1981)) (217 mg, 1.26 mmol) in THF (3 ml) and the mixture was stirred for 1 hour at 0° C. The reaction mixture was poured into phosphate buffer solution (35 ml, pH 7.0) and extracted with ether. After evaporation of the combined ether extracts, the oily residue was chromatographed on a silica gel column eluting with a mixture of hexane:ether:triethylamine (75:25:0.1) to afford 163 mg of the title compound; NMR (CDCl$_3$)δ: 0.7–2.5 (m, 31H, C$_{12}$H$_{25}$, —C$_3$H$_6$—), 2.77 (m, 1H, H$_5$), 3.3 (dd, 1H, H$_6$, $J_{6,5}=2$ Hz, $J_{6,7}=8$ Hz), 3.63 (s, 3H, CO$_2$CH$_3$), 5.0 (t, 1H, H$_7$, $J_{7,6}=J_{7,8}=8$ Hz) and 5.65 (dt, 1H, H$_8$, $J_{8,7}=J_{8,9}=8$ Hz).

Step 2

Methyl 5(S)-hydroxy-6(R)-(2-carbomethoxy-4-oxo-4H-1-benzopyran-7-yl)thio-7-cis-eicosaenoate Following the procedure of Step 1 of Example 3 but substituting an equivalent amount of methyl 5(S),6(S)-oxido-7-cis-eicosaenoate for methyl trans-5,6-oxido-7,9-trans-11,14-cis-eicosatetraneoate and substituting methyl 7-mercapto-4-oxo-4H-1-benzopyran-2-carboxylate for methyl 7-mercapto-8n-propyl-4-oxo-4H-1-benzopyran-2-carboxylate, there was obtained the title compound; NMR (CDCl$_3$)δ: 0.8–2.5 (m, 32H, C$_{12}$H$_{25}$, C$_3$H$_6$, OH), 3.67 (s, 3H, CO$_2$CH$_3$), 3.80 (m, 1H, H$_5$), 4.0 (s, 3M, CO$_2$CH$_3$), 4.27 (dd, 1H, H$_6$, $J_{6,5}=3$ Hz, $J_{6,7}=9$ Hz), 5.3–5.8 (m, 2H, H$_7$, H$_8$), 7.07 (s, 1H, H$_3$ (ar)), 7.37 (dd, 1H, H$_6$ (ar), $J_{6,5}=$b 9 Hz, $J_{6,8}=2$ Hz), 7.52 (d, 1H, H$_8$ (ar), $J_{8,6}=2$ Hz) 8.05 (d, 1H, H$_5$, $J_{5,6}=9$ Hz).

Step 3

5(S)-Hydroxy-6(R)-(2-carbomethoxy-4-oxy-4-oxo-4H-1- benzopyran-7-yl)thio-7-cis-eicosenoic acid Following the procedure of Step 2 of Example 3 but substituting the ester from Step 2 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, there was obtained the title compound; NMR (CD$_3$OD)δ: 0.8–2.3 (m, 31H, C$_{12}$H$_{25}$, —C$_3$H$_6$—), 3.90 (m, 1H, H$_5$), 4.35 (m, 1H, H$_6$), 5.4–5.7 (m, 2H, H$_2$, H$_8$), 6.97 (s, 1H, H$_3$ (ar)), 7.52 (dd, 1H, H$_6$ (ar), $J_{6,5}=9$ Hz, $J_{6,8}=2$ Hz), 7.75 (d, 1H, H$_8$ (ar), $J_{8,6}=2$ Hz) and 8.05 (d, 1H, H$_5$, $J_{5,6}=9$ 1 Hz).

EXAMPLE 13

Preparation of 5(S)-hydroxy-6(R)-(2-carboxy-4-oxo-4H-1-benzopyran-7-yl)thio-7-trans-9-cis-eicosadienoic acid

Step 1

Methyl 5(S),6(S)-oxido-7-trans-9-cis-eicosadienoate

Following the procedure of Step 1 of Example 12 but substituting an equivalent amount of methyl 8-formyl-5(S),6(S)-oxido-7-trans-octenoate (See, J. Rokach et al., *Tet. Lett.*, 22 2759-2762 (1981)) for methyl 6-formyl-5(S),6(S)-oxidohexanoate and substituting triphenyl undecanyl phosphonium bromide for triphenyl tridecanyl phosphonium iodide, there was obtained the title compound; NMR (CDCl$_3$)$\delta$: 0.8-2.5 (m, 27H, C$_{10}$H$_{21}$, —C$_3$H$_6$—), 2.83 (m, 1H, H$_5$), 3.12 (dd, 1H, H$_6$, J$_{6,5}$=2 Hz, J$_{6,7}$=8 Hz), 3.67 (s, 3H, CO$_2$CH$_3$), 5.1-5.6 (m, 2H, H$_7$, H$_{10}$), 5.97 (t, 1H, H$_9$, J$_{9,8}$=J$_{9,10}$=11 Hz) and 8.67 (dd. 1H, H$_8$, J$_{8,7}$=15 Hz, J$_{8,9}$=11 Hz).

Step 2

Methyl 5(S)-hydroxy-6(R)-(2-carbomethoxy-4-oxo-4H-1-benzopyran-7-yl)thio-7-trans-9-cis-eicosadienoate Following the procedure of Step 1 of Example 3 but substituting an equivalent amount of methyl 5(S),6(S)-oxido-7-trans-9-cis-eicosadienoate for methyl trans-5,6-oxido-7,9-trans-11,14-cis-eicosatetraenoate and substituting methyl 7-mercapto-4-oxo-4H-1-benzopyran-2-carboxylate for methyl 7-mercapto-8n-propyl-4-oxo-4H-1-benzopyran-2-carboxylate, there was obtained the title compound; NMR (CDCl$_3$)$\delta$: 0.8-2.5 (m, 28H, C$_{10}$H$_{21}$. —C$_3$H$_6$—, OH), 3.67 (s, 3H, CO$_2$CH$_3$), 3.80 (m, 1H, H$_5$), 4.00 (s, 3H, CO$_2$CH$_3$), 4.20 (m, 1H, H$_6$), 5.2-6.2 (m, 3H, H$_7$, H$_9$, H$_{10}$), 6.57 (dd, 1H, H, J$_{8,7}$=15 Hz, J$_{8,9}$=11 Hz), 7.03 (s, 1H, H$_3$ (ar)), 7.32 (dd, 1H, H$_6$ (ar), J$_{6,5}$=9 Hz, J$_{6,8}$=2 Hz), 7.5 (d, 1H, H$_8$ (ar), J$_{8,6}$=2 Hz) and 8.03 (d, 1H, H$_5$ (ar), J$_{5,6}$=9 Hz).

Step 3

5(S)-Hydroxy-6(R)-(2-carboxy-4-oxo-4H-1-benzopyran-7-yl)thio-7-trans-9-cis-eicosadienoic acid Following the procedure of Step 2 of Example 3 but substituting the ester from Step 2 above for methyl 5,6-erythro-5-hydroxy-6-(2-carbomethoxy-8n- propyl-4-oxo-4H-1-benzopyran-7-yl)thio-7,9-trans-11,14-cis-eicosatetraenoate, there was obtained the title compound; NMR CD$_3$OD)$\delta$: 0.7-2.2 (m, 27H, C$_{10}$H$_{21}$, —C$_3$H$_6$—), 3.82 (m, 1H, H$_5$), 4.08 (m, 1H, H$_6$), 5.25 (dt, 1H, H$_{10}$, J$_{10,9}$=11 Hz, J$_{10,11}$=8 Hz), 5.6 (dd, 1H, H$_7$, J$_{7,6}$=10 Hz, J$_{7,8}$=15 Hz), 6.82 (t, 1H, H$_9$, J$_{9,8}$=J$_{9,10}$=11 Hz), 6.37 (dd, 1H, H$_8$, J$_{8,7}$=15 Hz, J$_{8,9}$=11 Hz), 6.84 (s, 1H, H$_3$ (ar)), 7.35 (dd, 1H, H$_6$ (ar), J$_{6,5}$=9 Hz, J$_{6,8}$=2 Hz), 7.55 (d, 1H H$_8$ (ar), J$_{8,6}$=2 Hz) and 7.9 (d, 1H, H$_5$ (ar), J$_{5,6}$=9 Hz).

EXAMPLE 14

Preparation of methyl 7-mercapto-2-methoxyquinolin-3-carboxylate

Step 1

3-(((4-Methoxyphenyl)methyl)thio)aniline

Sodium ydride (99%, 8.22 g) was added in portions of a stirred solution of 3-aminothiophenol (44.23 g) in dry DMF (132 ml) at 0°. After 30 minutes a solution of 4-methoxybenzyl chloride (53.61 g) in acetonitrile (132 ml) was added dropwise and the mixture was stirred 30 minutes at 0° and 1 hour more at ambient temperature. The mixture was poured into ice-water (200 ml) and the resulting solid was collected by filtration and dried in air to provide the title compound, m.p. 85°-86°.

Step 2

N-(1,3-dioxo-3-ethoxy)propyl-3-(((4-methoxyphenyl)-methyl)thio)aniline

The amine from Step 1 (250 g) and diethyl malonate (1.25 l) were stirred under a N$_2$ stream at 170°-180° for 2.5 hours. The volatile components were removed by distillation in vacuo at 120°. The resulting melt was poured into t-butyl methyl ether (1 l) slowly with stirring, and the resulting solid was collected by filtration and washed with t-butyl methyl ether (250 ml) to provide the title compound, m.p. 81°-84°.

Step 3

Ethyl 2-chloro-7-(4-methoxyphenylmethylthio)quinolin-3-carboxylate

A mixture of oxalyl chloride (23.42 g) and DMF (13.48 g) in CH$_2$Cl$_2$ (500 ml) was prepared and cooled to 0°. The amide from Step 2 (33.1 g) was added and the mixture was stirred at ambient temperature for 48 hours. The mixture was reduced to dryness and chromatographed on silica gel (eluting with ethyl acetate:-hexane 1:1) to provide the title compound, m.p. 110°-112°.

Step 4

Methyl 2-methoxy-7-(((4-methoxyphenyl)methyl)thio)quinolin-3-carboxylate

The ester from Step 3 (7.76 g) was added to a solution of sodium (920 mg) in anhydrous methanol (50 ml) and the resulting suspension was refluxed under an argon atmosphere for 75 minutes. The mixture was cooled, diluted with CH$_2$Cl$_2$ (200 ml), washed with water (3×50 ml) and reduced to dryness to provide the title compound, m.p. 133°-134.5°.

Analysis, calculated: C, 65.01; H, 5.18; N, 3.79; S, 8.68. Observed: C, 65.07; H, 5.06; N, 3.72; S, 8.43.

Step 5

Methyl 7-mercapto-2-methoxyquinolin-3- carboxylate

A mixture of the ester from Step 4 (2.77 g), 90% formic acid (70 ml) and mercuric acetate (7.17 g) was stirred under an argon atmosphere at ambient temperature for 3 hours. The reaction mixture was poured into a mixture of water (350 ml) and CH$_2$Cl$_2$ (700 ml) and H$_2$S gas was passed through the vigorously stirred mixture for 5 minutes. The organic phase was separated, filtered through celite, washed with water, dried (MgSO$_4$) and reduced to dryness to provide the title compound, m.p. 103°-105°.

Analysis, calculated: C, 57.81; H, 4.45; N, 5.62; S, 12.86. Observed: C, 57.94; H, 4.40; N, 5.35; S, 12.81.

EXAMPLE 15

Preparation of 5,6-erythro-5-hydroxy-6-(3-carboxy-2-methoxyquinolin-7-yl)thio-7,9-trans-11,14-cis-eicosatetraenoic acid

Step 1

Methyl 5,6-erythro-5-hydroxy-6-(3-carbomethoxy-2-methoxyquinolin-7-yl)thio-7,9-trans-11,14-cis-eicosatetraenoate Following the procedure of Step 1 of Example 3 but substituting methyl 7-mercapto-2-methoxy quinolin-3-carboxylate (from Example 14) for methyl 7-mercapto-8n-propyl-4-oxo-4H-1-benzopyran-2-carboxylate, the title compound is obtained.

Step 2

5,6-Erythro-5-hydroxy-6-(3-carboxy-2-methoxyquinolin-7-yl)thio-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14-cis-eicosatetraneoate, the title compound is obtained.

EXAMPLE 16

Preparation of 5(S)-hydroxy-6(R)-(3-carboxy-2-methoxy quinolin-7-yl)thio-7-trans-9-cis-eicosadienoic acid

Step 1

Methyl 5(S)-hydroxy-6(R)-(3-carbomethoxy)-2-methoxyquinolin-7-yl)thio-7-trans-9-cis-eicosadienoate Following the procedure of Step 1 of Example 3 but substituting methyl 5(S), 6(S)-oxido-7-trans-9-cis-eicosadienoate (Example 13, Step 1) for methyl trans-5,6-oxido-7,9-trans-11,14-cis-eicosatetraenoate and substituting methyl 7-mercapto-2-methoxy quinolin-3-carboxylate (from Example 14) for methyl 7-mercapto-8n-propyl-4-oxo-4H-1-benzopyran-2-carboxylate, the title compound is obtained.

Step 2

5(S)-Hydroxy-6(R)-(3-carboxy-2-methoxy quinolin-7-yl)thio-7-trans-9-cis-eicosadienoic acid Following the procedure of Step 2 of Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14-cis eicosatetraneoate, the title compound is obtained.

EXAMPLE 17

Preparation of 5(S)-hydroxy-6(R)-(3-carboxy-2-methoxy quinolin-7-yl)thio-7-cis-eicosenoic acid

Step 1

Methyl 5(S)-hydroxy-6(R)-(3-carbomethoxy-2-methoxy quinolin-7-yl)thio-7-cis-eicosaenoate Following the procedure of Step 1 of Example 3 but substituting methyl 5(S), 6(S)-oxido-7-cis- eicosenoate (Example 12, Step 1) for methyl trans-5,6-oxido-7,9-trans-11,14-cis-eicosatetraenoate and substituting methyl 7-mercapto-2-methoxyquinolin-3-carboxylate (from Example 14) for methyl 7-mercapto-8n-propyl-4-oxo-4H-1-benzopyran-2-carboxylate, the title compound is obtained.

Step 2

5(S)-Hydroxy-6(R)-(3-carboxy-2-methoxyquinolin-7-yl)thio-7-cis-eicosaenoic acid

Following the procedure of Step 2 of Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14-cis-eicosatetraneoate, the title compound is obtained.

EXAMPLE 18

Preparation of methyl 7-mercapto-4-methyl-8n-propyl-2-oxo-2H-1-benzopyran-3-acetate

Step 1

Methyl 7-hydroxy-4-methyl-2-oxo-2H-1-benzopyran-3-acetate

7-Hydroxy-4-methyl-2-oxo-2H-1-benzopyran-3-acetic acid (see Chemical Abstracts 64, 15826f) was dissolved in a mixture of HCl (gas) (10 g) and anhydrous methanol (90 ml) and left 1 hour at room temperature. The resulting crystals were collected by filtration and washed with ether to provide the title compound, m.p. 194°–196°.

Step 2

Meth 1 7-allyloxy-4-methyl-2-oxo-2H-1-benzopyran-3-acetate

The ester from Step 1 (500 mg) was added to a suspension of NaH (98%, 58 mg) in anhydrous DMF (5 ml) and the mixture was stirred 30 minutes at ambient temperature. Allyl bromide (262 μl) was added and the mixture was heated at 70° for 3 hours. The mixture was cooled, poured into water (20 ml) and HCl (2 equivalents) and the solution was extracted with ether (2×50 ml). The extracts were washed with water (2×50 ml), dried ($Na_2SO_4$), reduced to dryness and chromatographed on silica gel (eluting with ethyl acetate-hexane 1:2) to provide the title compound, m.p. 72°–73°.

Analysis, calculated: C,66.66; H, 5.60. Observed: C, 66.73; H, 5.69.

Step 3

Methyl 7-hydroxy-4-methyl-8-allyl-2-oxo-2H-1-benzopyran-3-acetate

The ether from Step 2 (35.9 g) was refluxed in dichlorobenzene (50 ml) under $N_2$ atmosphere for 18 hour. The mixture was cooled, diluted with hexane and the resulting crystals were collected by filtration. Trituration with ether and filtration of the resulting solid gave the title compound, m.p. 160°–162°.

Analysis, calculated: C, 66.66; H, 5.60. Observed: C, 66.54; H, 5.45

Step 4

Methyl 7-hydroxy-4-methyl-8n-propyl-2-oxo-2H-1-benzopyran-3-acetate

The phenol from Step 3 (23 g) was hydrogenated in methanol (700 ml) under 50 psi $H_2$ pressure in the presence of 5% palladium on charcoal (2 g) for 1 hour. The catalyst was removed by filtration over celite and the solvent was removed to provide the title compound, m.p. 160°–162°.

Analysis, calculated: C, 66.19; H, 6.25.
Observed: C, 66.34; H, 6.04.

Step 5

Methyl 7-((dimethylamino)thioxomethoxy)-4-methyl-8n-propyl-2-oxo-2H-1-benzopyran-3-acetate Following the general procedure described in Example 1, Step 1, but substituting an equivalent amount of the phenol from Step 4 above for ethyl 7-hydroxy-8n-propyl-4-oxo-4H-1-benzopyran-2-carboxylate, there was obtained the title compound, m.p. 172°–173°.

Analysis, calculated: C, 60.46; H, 6.14; N, 3.71; S, 8.50. Observed: C, 60.46; H, 6.17; N, 3.71; S, 7.95.

Step 6

Methyl 7-(((dimethylamino)carbonylthio)-4-methyl-8n-propyl-2-oxo-2H-1-benzopyran)-3-acetate Following the general procedure described in Example 1, Step 2, but substituting an equivalent amount of the ester from Step 5 above for the title compound of Example 1, Step 1, there was obtained the title compound, m.p. 131°–132°.

Analysis, calculated: C, 60.46; H, 6.14; N, 3.71, S, 8.50. Observed: C, 60.57; H, 6.05; N, 3.69; S, 8.29.

Step 7

Methyl 7-mercapto-4-methyl-8n-propyl-2-oxo-2H-1-benzopyran-3-acetate

Following the procedure described in Example 1, Steps 3 and 4, but substituting the ester from Step 6 above for the title compound of Example 1, Step 2 and after chromatography of the collected solid on silica gel, there was obtained the title compound, m.p. 133°–134°.

Analysis, calculated: C, 62.72; H, 5.92; S, 10.47. Observed: C, 62.74; H, 5.68; S, 10.38.

EXAMPLE 19

Preparation of 5,6-erythro-5-hydroxy-6-(3-carboxy-methyl-4-methyl-8n-propyl-2-oxo-2H-1-benzopyran-7-yl)thio-7,9-trans-11,14-cis-eicosatetraenoic acid

Step 1

Methyl 5,6-erythro-5-hydroxy-6-(3-carbomethoxymethyl-4-methyl-2-oxo-8n-propyl-2H-1-benzopyran-7-yl)thio-7,9-trans-11,14-cis-eicosatetraenoate Following the procedure of Step 1, Example 3 but substituting methyl 7-mercapto-4-methyl-8n-propyl-2-oxo-2H-1-benzopyran-3-acetate (from Example 18) for methyl 7-mercapto-8n-propyl-4-oxo-4H-1-benzo-pyran-2-carboxylate, the title compound is obtained.

Step 2

5,6-Erythro-5-hydroxy-6-(3-carboxymethyl-4-methyl-8n-propyl-2-oxo-2H-1-benzopyran-7-yl)thio-7,9-trans-11,14-cis-eicosatetraenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate the title compound is obtained.

EXAMPLE 20

Preparation of 5(S)-hydroxy-6(R)-(3-carboxymethyl-4-methyl-8n-propyl-2-oxo-2H-1-benzopyran-7-yl)thio-7-trans-9-cis eicosadienoic acid

Step 1

Methyl 5(S)-hydroxy-6(R)-(3-carbomethoxymethyl-4-methyl-8n-propyl-2-oxo-2H-1-benzopyran-7-yl)thio-7-trans-9-cis-eicosadienoate Following the procedure of Step 1, Example 3 but substituting methyl 5(S),6(S)-oxido-7-trans-9-cis-eicosadienoate (Example 13, Step 1) for methyl trans-5,6-oxido-7,9-trans-11,14-cis-eicosatetraenoate and substituting methyl 7-mercapto-4-methyl-8n-propyl-2-oxo-2H-1-benzopyran-3-acetate (from Example 18 ) for methyl 7-mercapto-8n-propyl-4-oxo-4H-1-benzopyran-2-carboxylate, the title compound is obtained.

Step 2

5(S)-Hydroxy-6(R)-(3-carboxymethyl-4-methyl-8-n-propyl-2-oxo-2H-1-benzopyran-7-yl)thio-7-trans-9-cis-eicosadienoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 21

Preparation of 5(S)-hydroxy-6(R)-(3-carboxymethyl-4-methyl-8n-propyl-2-oxo-2H-1-benzopyran-7-yl)thio-7-cis-eicosenoic acid

Step 1

Methyl 5(S)-hydroxy-6(R)-(3-carbomethoxymethyl-4-methyl-8n-propyl-2-oxo-2H-1-benzopyran-7-yl)thio-7-cis-eicosenoate Following the procedure of Step 1 of Example 3 but substituting methyl 5(S),6(S)-oxido-7-cis-eicosenoate (Example 12, Step 1) for methyl trans-5,6-oxido-7,9-trans-11,14-cis-eicosatetraenoate and substituting methyl 7-mercapto-4-methyl-8n-propyl-2-oxo-2H-1-benzopyran-3-acetate (from Example 18) for methyl 7-mercapto-8n-propyl-4-oxo-4H-1-benzopyran-2-carboxylate, the title compound is obtained.

Step 2

5(S)-Hydroxy-6(R)-(3-carboxymethyl-4-methyl-8n-propyl-2-oxo-2H-1-benzopyran-7-yl)thio-7-cis-eicosenoic acid Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 22

Preparation of Methyl
4-oxo-4-(4-mercaptophenyl)butanoate

Step 1

4-Oxo-4-(4-methoxyphenyl)butanoic acid

Anisole (70.0 g) and succinic anhydride (65.0 g) were dissolved in 1,2-dichloroethane (1 liter) and the mixture was cooled to 0° C. To the resulting suspension there was added, in portions, $AlCl_3$ (172 g) and the resulting mixture was stirred with a mechanical stirrer for 1 hour. The mixture was then poured into a mixture of ice and water (about 1 liter) containing 50 ml of concentrated HCl. The resulting white solid was collected by filtration, washed with water and air dried to yield the title compound, m.p. 145°–147° C.

Step 2

Methyl 4-oxo-4-(4-hydroxyphenyl)butanoate

A mixture of the compound from Step 1 (77.3 g), 48% HBr (310 ml), and acetic acid (620 ml) was heated under reflux for 18 hours. The resulting mixture was cooled to room temperature and poured into 3 liters of water. The resulting solution was extracted with ethyl acetate (3×500 ml). The combined organic layers were washed with water (4×200 ml), dried over $Na_2SO_4$, the solvents were removed by evaporation and the residue was dissolved in 10% HCl/methanol (500 ml). After 10 hours at room temperature the volatile components were removed by evaporation in vacuo. The resulting residue was triturated with hexane to yield the title compound, m.p. 115°–116°.

Step 3

Methyl 4-oxo-4-(4-dimethylthiocarbamoyl-oxyphenyl)butanoate

A solution of the compound from Step 2 (25 g), in anhydrous dimethylformamide (300 ml) was cooled to 0° and 99% NaH (3.46 g), was added in two portions. The mixture was stirred for 1 hour at 0° then dimethylthiocarbamoyl chloride (19.3 g) was added and the mixture heated at 90° under a $N_2$ atmosphere for 1.5 hours. The mixture was cooled to room temperature and diluted with water to 1,200 ml. The resulting solution was then extracted with ethyl acetate (3×50 ml). The combined organic layers were washed with brine and then dried over $Na_2SO_4$ and evaporated to dryness in vacuo to yield a residue which was purified by chromatography on silica gel to yield the title compound, m.p. 62°–64°.

Step 4

Methyl 4-oxo-4-(4-dimethylcarbamoylthiophenyl)butanoate

The compound from Step 3 (29.6 g) was heated neat at 200° for 10 hours under an $N_2$ atmosphere. The reaction was cooled to room temperature, dissolved in methylene chloride and purified by chromatography on silica gel to provide the title compound, m.p. 98°–100°.

Step 5

Methyl 4-oxo-4-(4-mercaptophenyl)butanoate

Sodium (280 mg) was dissolved in anhydrous methanol (50 ml) under a $N_2$ atmosphere. To the resulting solution there was added 5.0 g of the compound from Step 4. The mixture was stirred at room temperature overnight, then poured into a mixture containing 30 ml of water and 7 ml of concentrated HCl. The resulting yellow solid was collected by filtration, washed with water and dried in air to give the title compound, m.p. 83°–84°.

EXAMPLE 23

Preparation of 5,6-erythro-5-hydroxy-6-(4-(3-carboxypropanoyl)-phenyl)thio-7,9-trans-11,14-cis-eicosatetraenoic acid

Step 1

Methyl 5,6-erythro-5-hydroxy-6-(4-(3-carbomethoxy propanoyl)phenyl)thio-7,9-trans-11,14-cis-eicosatetraenoate Following the procedure of Step 1, Example 3 but substituting methyl 4-oxo-4-(4-mercaptophenyl) butanoate (from Example 22) for methyl 7-mercapto-8n-propyl-4-oxo-4H-1-benzopyran-2-carboxylate, the title compound is obtained.

Step 2

5,6-Erythro-5-hydroxy-6-(4-(3-carboxypropanoyl)-phenyl)thio-7,9-trans-11,14-cis-eicosatetraenoic acid Following the procedure of Step 2, Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14cis-eicosatetraenoate, the title compound is obtained.

EXAMPLE 24

Preparation of 5(S)-hydroxy-6(R)-(4-(3-carboxypropanoyl)-phenyl)thio-7-trans-9-cis-eicosadienoic acid

Step 1

Methyl 5(S)-hydroxy-6(R)-(4-(3-carbomethoxypropanoyl)-phenyl)thio-7-trans-9-cis-eicosadienoate Following the procedure of Step 1, Example 3 but substituting methyl 5(S),6(S)-oxido-7-trans-9-cis-eicosadienoate (Example 13, Step 1) for methyl trans-5,6-oxido-7,9-trans-11,14-cis-eicosatetraenoate and substituting methyl 4-oxo-4-(4-mercaptophenyl) butanoate (from Example 22) for methyl 7-mercapto-8n-propyl-4-oxo-4H-1-benzopyran-2-carboxylate, the title compound is obtained.

Step 2

5(S)-Hydroxy-6(R)-(4-(3-carboxypropanoyl)-phenyl)thio-7-trans-9-cis-eicosadienoic acid Following the procedure of Step 2, of Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14-cis-eicosatetraenoate, the title compound is obtained.

EXAMPLE 25

Preparation of
5(S)-hydroxy-6(R)-(4-(3-carboxypropanoyl)-
phenyl)thio-7-cis-eicosenoic acid

Step 1

Methyl
5(S)-hydroxy-6(R)-(4-(3-carbomethoxypropanoyl)-
phenyl)thio-7-cis-eicosenoate Following the procedure of Step 1, Example 3 but substituting methyl 5(S),6(S)-oxido-7-cis-eicosenoate (Example 12, Step 1) for methyl trans-5,6-oxido-7,9-trans-11,14-cis-eicosatetraenoate and substituting methyl 4-oxo-4-(4-mercaptophenyl) butanoate (from Example 22) for methyl 7-mercapto-8n-propyl-4-oxo-4H-1-benzopyran-2-carboxylate, the title compound is obtained.

Step 2

5(S)-Hydroxy-6-(R)-(4-(3-carboxypropanoyl)-
phenyl)thio-7-cis-eicosenoic acid

Following the procedure of Step 2 of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 26

Preparation of ethyl 3-oxo-3-(3-mercaptophenylamino) propanoate

A mixture of 3-aminothiophenol (5.0 g) and diethyl malonate (6.41 g) was heated under a nitrogen atmosphere for 2 hours at from 165° to 170° C. The mixture as chromatographed on silica gel to yield the title compound, m.p. 52°–54°.

Analysis, calculated: C, 55.21; H, 5.47; N, 5.85, S, 13.39. Observed: C, 54.64; H, 5.41; N, 5.80; S, 13.02.

EXAMPLE 27

Preparation of
5,6-erythro-5-hydroxy-6-(3-carboxyacetamido-
phenyl)thio-7,9-trans-11,14-cis-eicosatetraenoic acid

Step 1

Methyl
5,6-erythro-5-hydroxy-6-(3-carbethoxyacetamido-
phenyl)thio-7,9-trans-11,14-cis-eicosatetraenoate Following the procedure of Step 1, Example 3 but substituting ethyl 3-oxo-3-(3-mercaptophenylamino) propanoate (from Example 26) for methyl 7-mercapto-8n-propyl-4-oxo-4H-1-benzopyran-2-carboxylate, the title compound is obtained.

Step 2

5,6-Erythro-5-hydroxy-6-(3-carboxyacetamido-
phenyl)thio-7,9-trans-11,14-cis-eicosatetraenoic acid Following the procedure of Step 2, of Example 3 but substituting the ester from Step 1 above for methyl 5,6-erythro-5-hydroxy-6-(2-carbomethoxy-8n-propyl-4-oxo-1-benzopyran-7-yl)thio 7,9-trans-11,14-cis-eicosatetraenoate, the title compound is obtained.

EXAMPLE 28

Preparation of
5(S)-hydroxy-6(R)-(3-carboxyacetamidophenyl)thio-7-
trans-9-cis-eicosadienoic acid

Step 1

Methyl
5(S)-hydroxy-6(R)-(3-carbethoxyacetamido-
phenyl)thio-7-trans-9-cis-eicosadienoate Following the procedure of Step 1, Example 3 but substituting methyl 5(S),6(S)-oxido-7-trans-9-cis-eicosadienoate (Example 13, Step 1) for methyl trans-5,6-oxido-7,9-trans-11,14-cis-eicosatetraenoate and substituting ethyl 3-oxo-3-(3-mercaptophenylamino) propanoate (from Example 26) for methyl 7-mercapto-8n-propyl-4-oxo-4H-1-benzopyran-2-carboxylate, the compound is obtained.

Step 2

5(S)-Hydroxy-6(R)-(3-carboxyacetamidophenyl)-thio-
7-trans-9-cis-eicosadienoic acid Following the procedure of Step 2, of Example 3 but substituting the ester from Step 1 above for methyl 5,6-erythro-5-hydroxy-6-(2-carbomethoxy-8n-propyl-4-oxo-1-benzopyran-7-yl)thio-7,9-trans-11,14-cis-eicosatetraenoate, the title compound is obtained.

EXAMPLE 29

Preparation of
5(S)-hydroxy-6(R)-(3-carboxyacetamidophenyl)thio-7-
cis-eicosenoic acid

Step 1

Methyl
5(S)-hydroxy-6(R)-(3-carbethoxyacetamido-
phenyl)thio-7-cis-eicosaenoate

Following the procedure of Step 1, Example 3, but substituting methyl 5(S), 6(R)-oxido-7-cis-eicosaenoate (Example 12, Step 1) for methyl trans-5,6-oxido-7,9-trans-11,14-cis-eicosatetraenoate and substituting ethyl 3-oxo-3-(3-mercaptophenylamino) propanoate (from Example 26) for methyl 7-mercapto-8n-propyl-4-oxo-4H-1-benzopyran-2-carboxylate, the title compound is obtained.

Step 2

5(S)-Hydroxy-6(R)-(3-carboxyacetamidophenyl)-thio-
7-cis-eicosaenoic acid

Following the procedure of Step 2, of Example 3 but substituting the ester from Step 1 above for methyl 5,6-erythro-5-hydroxy-6-(2-carbomethoxy-8n-propyl-4-oxo-4H-1-benzopyran-7-yl)thio-7,9-trans-11,14-cis-eicosatetraenoate, the title compound is obtained.

EXAMPLE 30

Preparation of 1-t-butyldimethylsiloxyhex-5-yne

To a solution of 5-hexyn-1-ol (9.81 g) in dichloromethane (50 ml) was added, at 0° C., triethylamine (10 ml), t-butyldimethylsilylchloride (17 g) and 4-dimethylaminopyridine (100 mg) and the mixture was stirred 16 hrs. while warming to room temperature. Dichloromethane (100 ml) was added and the organic layer was washed with 1N HCl (2×50 ml), brine and dried with $Na_2SO_4$. Solvents were removed and residue distilled under vacuum to yield the title compound as an oil (19 g, 89%).

p.m.r.(90 MHz, CDCl$_3$) δ: 3.55, 2H(m); 2.0–2.25, 2H(m); 1.8–1.9, 1H(m); 1.4–1.7, 4H(m); 0.8–0.9, 9H(bs)

EXAMPLE 31

Preparation of 1-t-butyldimethylsiloxyeicosa-5(E)-ene-7-yne

To 1-t-butyldi-methylsiloxyhex-5-yne (title compound of Example 30) (1.06g.) in THF (tetrahydrofuran) (5 ml) was added disamylborane (5 mM) and the mixture stirred one hour at 0° C. for one hour. It was cooled to −78° C. and added to a suspension of lithium tetradecyne at −78° C. (5 mM) and the mixture was stirred 16 hours while coming to room temperature. It was then cooled to −78° C. and iodine (1.26 g.) in diethylether (15 ml) was added. The mixture was allowed to warm to room temperature, then washed with 3N NaOH (50 ml) containing a saturated solution of Na$_2$S$_2$O$_3$ (5 ml). To the separated organic layer was added 3N NaOH (1.7 ml) and 30% H$_2$O$_2$ (1.5 ml) and the mixture stirred for 2 hours. The aqueous layer was saturated with K$_2$CO$_3$, stirred ½ hour and Na$_2$SO$_4$ was added. It was extracted with diethyl ether and the organic layer was washed with brine and dried with Na$_2$SO$_4$. Removal of the solvents yielded the compound which was purified on flash chromatography (1.48 g., 73%).

p.m.r. (90 MHz, CDCl$_3$)≃: 5.8–6.2 1H(m); 5.1–5.6, 1H(m); 3.45–3.7. 2H(bt); 2.4–0.8m(46H).

EXAMPLE 32

Preparation of Methyl trans-5-ene-7-yne-eicosanoate

To a cooled, 0° C. solution of 1-t-butyldimethylsiloxyeicosa-5(E)-ene-7-yne (title compound of Example 31) (808 mg) in acetone (20 ml) was added 8N Jones' Reagent (1.25 ml) and the mixture was stirred at 0° C for 1 hour; NaHSO$_3$ (1 g) was added and the mixture was stirred 15 minutes. The mixture was filtered, evaporated to dryness and the residue taken in ethyl ether (25 ml), washed with 1N HCl (25 ml), brine (25 ml) and dried with Na$_2$SO$_4$. Solvents were removed and the residue taken in ethyl ether (10 ml) and cooled to 0° C.; excess diazomethane (in ethyl ether) was added. Solvents were removed and the residue purified on flash chouromatography to yield the title compound (356 mg, 56%).

p.m.r (90 MHz, CDCl$_3$)δ: 5.8–6.2 1H(m); 5 15–5.6, 1H(m); 3.65, 3H(s); 2.4–1.1 28H(m); 0.75–0.95, 3H(bt).

EXAMPLE 33

Preparation of Methyl trans-5,6-epoxy-7-yne-eicosanoate

To a cooled (0° C.) solution of methyl trans 5-ene-7-yne-eicosanoate (title compound of Example 32) (30 mg) in chloroform (5 ml) was added m-chloroperoxybenzoic acid (37 mg) and the suspension was stirred for 16 hours at 0° C. Ca(OH)$_2$ (40 mg) was then added and the suspension was stirred for 1 hour. Thereafter, insolubles were filtered and solvents removed. The residue was purified by chromatography to yield the title compond as an oil (20 mg, 66%).

Analysis: Calculated: C, 74.95; H, 10.78.
Found: C, 74.66; H, 10.87.

EXAMPLE 34

Preparation of Dimethyl (5S, 6R) and (5R, 6S)-5-hydroxy-6-[7'-thio-(4'-oxo-4-H-1'-benzopyran-2'-carboxylate)]eicos-7-ynoate.

To a solution of methyl trans 5,6-epoxy-7-yne-eicosanoate (title compound of Example 33) (168 mg), triethylamine (85μL) and methanol (5 ml) was added the thiol of Example 2 (177 mg) and the mixture was stirred for 2 hours at room temperature. It was then cooled to 0° C. and filtered on a Buchner funnel. The crystals were dried to yield the title compound (220 mg, 77%).

Analysis: Calculated: C, 67.11; H, 7.74; S, 5.60. Found: C, 67.16; H, 8.02; S, 5.79.

EXAMPLE 35

Preparation of Disodium (5S 6R) and (5R, 6S) 5-hydroxy-6-[7'-thio-(4'-oxo-4-H-1'-benzopyran-2'-carbo xylate]-7-yne-eicosanoate, monohydrate.

A solution of the title compound of Example 34 (371 mg), methanol (7 ml). 1M Na$_2$CO$_3$ (3.5 ml) and THF (7 ml) was stirred at 0° C until thin layer chromatography showed the hydrolysis was complete; volatiles were removed and the residue purified on a XAD-8 resin to yield the title compound as a beige-yellow foam (100).

Analysis: Calculated: C. 59.39; H, 6.64; S, 5.28. Found: C, 59.73; H, 6.99; S, 5.64.

EXAMPLE 36

Preparation of Methyl (5S, 6R) and (5R, 6S)-5-hydroxy-6-S-(methyl N-trifluoroacetylcysteinylygly-cinate)-7-eicosynoate.

To the title compound of Example 33 (168 mg) in methanol (5 ml) and triethylamine (85 μL) was added methyl N-trifluoroacetyl cysteinyl-glycinate (172 mg) and the mixture was stirred at room temperature for 12 hours. Filtration, evaporation of the solvents and purification by flash chromatography yielded a mixture of the diastereoisomers which were separated on HPLC (μ-Porasil) to yield isomer A (65 mg) and isomer B (65 mg).

isomer A [5R, 6S]:
p.m.r. 250 MHz) δ: 8.0 1H (bd); 7.25, 1H(bt); 4.8, 1H(q); 4.0–4.25, 2H(m); 3.6, 3H(s); 3.4, 3H (s); 3.0–3.45, 3H(m); 2.4, 2H, (t); 2.25, 2H(t); 0 .8–2, 29H(m).

Isomer B [5S, 6R]:
p.m.r. (250 MHz)δ7.8, 1H(bd); ;7.1, 1H(bt); 4.85, 1H(q); 4.1, 2H(m); 3.8. 3H(s); 3.7. 3H(s); 2.5–2.9. 3H(m); 2.4. 2H(t); 2.3, 2H(t); 0.8–2, 29H(m)

EXAMPLE 37

Preparation of (5R, 6S) (Isomer A) and (5S, 6R) (Isomer B) Di-sodium 5-hydroxy-6-S-(cysteinyl glycinyl)-7-eicosynoate To each of the title compounds of Example 36 in methanol and THF, add 1M Na$_2$CO$_3$ and stir at 0° C. for several hours. Remove the solvents and purify the residue on XAD-8 resin to yield the title compounds.

EXAMPLE 38

Preparation of ethyl (5S,6S)-oxido-eicosa-7-yn-oate and ethyl (5S,6R) oxido eicosa-7-yn-oate.

To 1-tetradecyne (600 mg, 3 mM) in THF(20 ml) at −78° was added n-butyllithium (1.8 ml of 1.5M solution) dropwise over 5 minutes. The reaction mixture was stirred 1 hour at −78° and then ethyl 5(S) benzoyloxy-6-oxohexanoate (0.8 g, 2.9 mM) in tetrahydrofuran (5 ml) was added dropwise. After 1 hour at −78°, methanesulphonyl chloride (30µl ) and triethylamine (300µ) was added. The reaction mixture was stirred 1 hour at −78° then warmed to room temperature (1 hour). Sodium ethoxide (15 ml of 0.5M solution) was added and the reaction stirred 1 hour at room temperature. The reaction mixture was partitioned between pH7 buffer (25% ammonium acetate) and ether. The ether phase was dried and evaporated. Purification using Waters Prep. 500 (5% ethylacetate/hexane) afforded 250 mg trans epoxide and 60 mg cis epoxide.

p.m.r. (90 MHz) of trans epoxideδ: 0.9(t,3H), 1.0–2.0(m,27H), 2.0–2.5(m, 4H), 3.0(m,1H), 3.15(m, 1H), 4.15 p.p.m(q,2H).

p.m.r. (90MHz) of cis epoxideδ: 0.9(t, 3H), 1.0–2.0(m, 28H), 2.2–2.6(m, 4H), 3.15(m, 1H), 3.5(m, 1H) and 4.2 p.p.m.(q,2H).

EXAMPLE 39

Preparation of Ethyl (5S, 6R) -5- hydroxy-6-S-(methyl N- trifluoroacetylcysteinylglycinate)-eicosa-7-yn-oate.

The trans epoxide of Example 38 (50 mg), methyl N-trifluoroacetylcysteinylglycinate (50 mg) and triethylamine (2 drops) were stirred overnight in 0.5 ml ethanol. Chromatography using ethyl ether/hexane (40% v/v) afforded 50 mg (50%) of coupled product.

p.m.r. (250 MHz, CDCl$_3$)δ: 0.9(t, 3H), 1.0–2.0(m, 28H), 2.15(m, 2H), 2.25(m, 2H), 2.6(m,1H), 3.0(m, 1H), 3.25(m, 1H), 3.7(m, 4H), 4.1(m, 4H), 4.8(q. 1H), 7.3(m, 1H) and 7.8 p.p.m. (m, 1H).

EXAMPLE 40

Preparation of (5S, 6R)-5-hydroxy-6-5-(cysteinylglycne)-eicosa-7-ynoic acid di-sodium salt.

The title compound of Example 39 was hydrolyzed by dissolving 50 mg in methanol (10 ml) and water (1 ml) containing sodium carbonate (50 mg) and stirring at 5° for 5 days. The solvents were evaporated and the residue purified by high performance liquid chromatography (HPLC) (usin C$_{18}$ µ-bondapak columns) with H$_2$O-Methanol (1:4) at pH 5.6, followed by desalting on an XAD-8 resin column to obtain the title compound.

p.m.r. (250 MHz, DMSO/D$_2$O )δ: 0.9(t,3H), 1.0–1.8(m, 28H) 2.1(m, 2H), 2.4(m, 2H), 2.6(d, 1H) 2.7(dd, 1H), 2.9(dd, 1H) 3.5(m, 1H), 3.7(m, 1H), and 3.9(m, 2H).

EXAMPLE 41

Preparation of ethyl 5S-hydroxy-6R-[7′-thio-(4′-oxo-4H-1′-benzopyran-2′-methyl carboxylate)]-eicosa-7-ynoate Treatment of the trans epoxide of Example 38 with the thiol of Example 2 as described in Example 39 afforded the title compound in 75% yield.

p.m.r. (250 MHz CDCl$_3$)δ: 0.85(t, 3H), 1.0–1.9(m, 27H), 2.15(dt, 2H), 2.35(dt, 2H), 3.9(m, 1H), 4.0(m, 4H), 4.1(m, 3H) 7.15(s, 1H), 7.35(dd, 1H), 7.6(m, 1H) and 8.05 p.p.m. (d, 1H).

EXAMPLE 42

Preparation of 5S-hydroxy-6R-[7′-thio-(4′-oxo-4H-1′-benzopyran-2′carboxylic acid)]-eicosa-7-acid di-sodium salt.

Hydrolysis of the diester of Example 41 using Na$_2$CO$_3$/methanol/H$_2$O as described in Example 40 afforded the disodium salt in 93% yield.

p.m.r. (250 MHz, D$_2$O )δ: 0.85(m, 3H). 1.0–1.8(m, 27H), 1.90(m, 2H), 2.15(m, 2H), 3.75(m, 1H), 4.35(m, 1H), 6.6(s, 1H), 7.3(dd, 1H), 7.6(s, 1H), and 7.85 p.p.m. (d, 1H).

EXAMPLE 43

Preparation of ethyl 5S-Hydroxy-6R-(3′-carbomethoxy-2′-methoxyquinol-7′-ylthio)-eicosa-7-ynoate Reaction of the trans epoxide from Example 38 with the thiol from Example 14 according to the procedure of Example 39 gave the title compound in 88% yield.

p.m.r. (250 MHz, acetone-d$_6$)δ: 0.87(t,3H), 1.1–2.0 (m, 27H), 2.18(td, 2H), 2.35(t, 2H), 2.95(d, 1H), 3.88(s, 3H), 4.08(s, 3H) and (q, 2H) 4.35(m, 1H), 7.46(dd, 1H), 7.83(m, 2H), 8.58(s, 1H).

EXAMPLE 44

Preparation of 5S-hydroxy-6R-(3′-carboxy-2′-methoxy quinol-7′-ylthio)-eicosa-7-ynoic acid disodium salt.

Hydrolysis of the title compound of Example 43 according to the procedure of Example 40 but using NaOH in place of Na$_2$CO$_3$ afforded the title compound in 95% yield. Analysis:

| ELEMENTS | CALCULATED (for C$_{31}$H$_{41}$NO$_6$SNa$_2$) | FOUND |
|---|---|---|
| Carbon | 61.9 | 61.69 |
| Hydrogen | 6.9 | 7.00 |
| Nitrogen | 2.3 | 2.28 |
| Sulphur | 5.3 | 5.00 |

EXAMPLE 45

Preparation of 1-(Trimethylsilyl) tetradec-3(E)-ene-1-yne.

To a cold (−78° C.) suspension of 1-trimethylsilyl-3-propynyl phosphonium bromide (8.80 g, 19.4 m mol) in THF (100 ml) was added n-BuLi(n-butyl lithium)(12.0 ml of 1.6M in hexane) dropwise over 5 minutes. The resulting red-brown solution was stirred at −40° C. for 30 minutes and cooled again to −78° C. Then, undecaldehyde (3.3 ml, 16.0 mmol) solution in THF (20 ml) was added dropwise to the cold ylid solution. After completion of the addition, the −78° C. bath was replaced by an ice/water bath. After 1 hour, pentane (600 ml) was added and the resulting suspension was filtered over silica. The solid was washed with pentane (100 ml), the filtrate evaporated, dissolved in pentane (600 ml) and filtered a second time over silica. Evaporation afforded 3.63 g. (86%) of a mixture of cis and trans isomers of the title compound in a ratio of 1 to 7 respectively. $^1$H NMR (250 MHz CDCl$_3$) of trans isomer : 0.15 (s, 9H,), 0.85 (t, 3H), 1.25 (m, 16H, 2.05 (qd, 2H), 5.47 (dt, 1H,), 6.19 (dt, 1H).

EXAMPLE 46

Preparation of Tetradec-3(E)-ene-1-yne

To a vigorously stirred solution of the title compound of Example 45 (1.4 g 53 mmol) in DMF (dimethylformamide) (45 ml) was added $KF \cdot 2H_2O$-(1.5 g, 150 mmol). After 1.5 hours, the reaction was poured in brine/water (500 ml of 1 to 1) and ethyl ether was added. The organic layer was separated and the aqueous phase was extracted twice with ethyl ether (2×100 ml). The combined organic phases were dried ($MgSO_4$), filtered and evaporated to afford 1.0 g (quantitative) of the title compound. $^1H$ NMR (250 MHz, $CDCl_3$)δ: 0.87(S, 3H, $CH_3$), 1.25(m, 16H), 2.10 (td, 2H), 2.78(d, 1H), 5.43(dm, 1H), 6.24(dt, 1H).

EXAMPLE 47

Preparation of ethyl (5S, 6S)-oxido-eicosa-9(E)-ene-7-yn-oate

Following the procedure of Example 38, but substituting the title compound of Example 46 for 1-tetradecyne, afforded product in 14% yield [α]-8.9 (c=1.0, $CDCl_3$). $^1H$ NMR (250 MHz, Acetone $d_6$)δ: 0.9 (t, 3H), 1.0–1.8(m, 23H), 2.0–2.4(m, 4H) 3.05(m, 1H), 3.25(m, 1H), 4.08(q, 2H), 5.53(dm, 1H) 6.18(dt, 1H). High resolution Mass spec. m/e: 348.2661→$C_{22}H_{36}O_3$.

EXAMPLE 48

Preparation of Ethyl (5S, 6R) -5- hydroxy-6-S-(methyl N-trifluoroacetyl-2-cysteinylglycinate)-eicosa-7-yn-9(E)-enoate Following the procedure of Example 39, but substituting the title compound of Example 47 for the transepoxide of Example 38, afforded the title compound in 89% yield $[\alpha]_D = +3.4°$ (c=1.0, $CDCl_3$).
p.m.r. (250 MHz, $CDCl_3$)δ: 0.9(t, 3H), 1.0–1.6(m, 24H), 0.6–2.0(m, 4H), 2.1(m, 2H), 2.4(m, 2H), 2.6(d, 1H), 8.0(dd, 1H), 3.3(dd, 1H), 3.8(t, 3H), 3.9(m, 1H), 4.2(m, 4H), 4.8(q, 1H), 5.5(d, 1H), 6.2(dt, 1H)), 7.1(t, 1H) and 7.7 p.p.m. (1H).

EXAMPLE 49

Preparation of (5S, 6R)-5-hydroxy-6-S-( cysteinylglycyl) eicosa-7-yn-9E-enoic acid di-sodium salt.

The title compound of Example 48 (55 mg) and $Na_2CO_3$ (50 mg) were stirred for 5 days at 5° C. in methanol (10 ml) and water (1 ml). The solvents were evaporated. Purification by HPLC. (μ-bondapak $C_{18}$ using $H_2O$ methanol (1:4) with the PH at about 5.6 afforded product which was desalted using an XAD-8 column to yield 30 mg (64%) of the title compound.
p.m.r. (250 MHz, $DMSO/D_2O$ ) δ: 0.9(t, 3H). 1.0–1.7(m, 28H), 2.0(m, 4H), 2.6(m, 1H), 2.7(m, 1H), 2.7(m, 1H), 2.9(m, 1H), 3.4(m, 1H). 3.6(m, 1H), 3.9(m, 2H), 5.5(d, 1H), and 6.1 p.p.m. (dt. 1H).

EXAMPLE 50

Preparation of Ethyl 5S-Hydroxy-6R-(3'carboxymethyl-2-methoxyquinol-7'-ylthio)-eicosa-9(E)-ene-7-yuoate The title compound of Example 47 was opened with the thiol of Example 14 as descibed in Example 39 to give the di-ester in 76% yield $[\alpha]_D$-238(c=1.0 in $CHCl_3$).

$^1H$ NMR (250 MHz $CDCl_3$) δ: (t, 3H), 1.1–1.95(m, 23H), 2.05(td, 2H), 2.35(t, 2H), 3.80(m, 1H), 3.92(S, 3H), 4.10(q, 2H), 4.13(s, 3H), 4.25(m, 1H), 5.45(d, 1H), 6.12(dt, 1H), 7.41(dd, 1H), 7.68(d, 1H), 7.89(d, 1H), 8.52(s, 1H),

EXAMPLE 51

Preparation of 5S-hydroxy-6R-(3'-carboxy-2'-methoxy quinol-7'-ylthio)-eicosa-7-yn-9(E)-enoic acid disodium salt Following the method of Example 44, hydrolysis of the title compound of Example 50 afforded the title compound in 91% yield. Analysis:

| ELEMENTS | CALCULATED | FOUND |
|---|---|---|
| Carbon | 60.3 | 60.26 |
| Hydrogen | 6.7 | 7.06 |
| Nitrogen | 2.3 | 2.20 |
| Sulphur | 5.2 | 5.28 |

EXAMPLE 52

Prearation of ethYl 2(E), 4(E)-Pentadecadienoate.

To a solution of potassium hexamethyldisilazide in toluene (0.62M, 184 ml) in THF (200 ml) was added a solution of triethyl 4-phosphonocrotonate (28.5 g) in THF(50 ml) at −70° C. in an atmosPhere of $N_2$. The solution was stirred for 15 minutes and a solution of undecylic aldehyde (17 g) in THF (50 ml) was added. The mixture was alloWed to warm to room temerature over 1 hour. The reaction mixure was quenched by the addition of saturated aqueous $NH_4Cl$ and the product was extracted in ether. The ether extract was chromatographed on a short column of silica gel using hexane-ether (95:5) as eluant to give a yellow oil (15.6 g) which was purified on Waters 500 PREP-LC using hexane-ether (10:2.5) to give the title compound as a colorless oil (12.9 g, 48%). Analysis calculated d for $C_{17}H_{30}O_2$: C, 76.64; H, 11.35. Found: C, 76.37; H, 11.34.

EXAMPLE 53

Preparation of 1-hydroxy-2(E), 4(E)-pentadecadiene

A solution of the title compounl of Example 52 (12.2 g) in THF (50 ml) was added to a suspension of $AlH_3.\frac{1}{3}$ ethyl ether (3.3 g in THF (50 ml)) at 0° C. in an atmosphere of $N_2$. The mixture was stirred at room temperature for 15 minutes and quenched with saturated aqueous $NH_4Cl$ solution. The mixture was extracted twice with ether and the combined extracts were washed with brine, dried over $Na_2SO_4$ to give a white solid (9.0 g), (88%). m.p. 37°–39° C.

EXAMPLE 54

Preparation of 1-bromo-2(E), 4(E)-pentadecadiene.

To a solution of the title compound of Example 53 6.5 g) and $CBr_4$ (9.7 g) in $CH_2Cl_2$ (50 ml) at 0° C. was added a solution of DIPHOS (1.2-bis(diphenylphosphino)ethane)(10.9 g) in $CH_2cl_2$(50 ml). The mixture was stirred for 2 hours at room temperature under $N_2$. Then the mixture was diluted with hexane (500 ml) and the suspension was chromatographed on a column of silica gel (70–230 mesh) eluting with 10% ether in hexane to give the title compound as an oil (4.2 g, 50%)). $^1H$ NMR($CDCl_3$)δ: 0.86(3H, t), 1.25(16H, s(6)). 2.1(2H, q), 4.05(2H, d), 5.7–5.9(2H, m), 5.95–6.1(1H, m), 6.15–6.35(1H, m).

EXAMPLE 55

Preparation of methyl (±)-trans-5,6-oxido-7(E), 9eicosadienoate

A mixture of the title compound of Example 54 (4.1 g) and tetrahydrothiophene (8 ml) in a mixture of ethanol (9 ml) and water (1 ml) was stirred at room temperature overnight and evaporated to dryness. A solution of methyl 4-formyl butyrate (2.4 g) and benzyltriethyl ammonium chloride (300 mg) in $CH_2Cl_2$ (30 ml) was added to the salt which was cooled to $-20°$ C. Thereafter, 10N NaOH (30 ml) was added at $-20°$ C and the mixture was stirred for 5 minutes. The mixture was extracted with ether and passed through a column of silica gel (packed with 20% triethylamine in hexane) eluted with hexane-ether-triethylamine (10;1;0.1) to give an oil as a mixture of cis and trans epoxides (2.3 ). The oil was dissolved in a small amount of hexane and left at $-7°$ C. overnight to afford the title compound as a white solid. 1H NMR $(CDCl_3)\delta$: characteristic peaks: 2.8–2.9(1H, m), 3.05–3.15(1H, dd), 3.68(3H,s), 5.2–5.3(1H, q) 5.65–5.85(1H, m), 5.95–6.10(1H, m), 6.32–6.42(1H, q).

EXAMPLE 56

Preparation of dimethyl (5S, 6R) and (5R, 6S) 5-hydroxy-6[7'-thio-(4'-oxo-4H-1'-benzopyran-2'-carboxylate)]-7(E), 9(E)-eicosadienoate To a solution of the title compound of Example 55 (200 mg) and the title compound of Example 2, Step 4, (280 mg) in a mixture of ethanol (120 μl) and $CH_2CL_2$(5 ml) were added 2, 2, 6, 6-tetramethyl-4-hydroxy piperidine-N-oxide radical (5 mg) and triethylamine (120 μl). The mixture was stirred at room temperature for 1 hour, ether (10 ml) was added and the mixture was passed through three Sep-pak columns which had been washed with (1:1) hexane-triethylamine (10 ml), eluting with hexane-ether (1:1). The crude compound was chromatographed on a column of silica gel (70–230 mesh) eluting with ether to give an oil which was crystallized from ether-hexane to give the title compound as a solid (180 mg, 53%). Analysis Calculated for $C_{32}H_{44}O_7S$: C, 67.10; H, 7.74; S, 5.60. Found: C, 67.66; H, 7.80; S, 5.37.

EXAMPLE 57

Preparation of (5S, 6R) and (5R, 6S) 5-hydroxy-6-[7'-thio-(4'-oxo-4H-1'-benzopyran-2'-carboxylic acid)]-7(E), 9(E)-eicosadienoic acid disodium salt.

To a solution of the title compound of Example 56 (215 mg) in THF (4 ml) at 0° C. under argon was added 0.2N NaOH (4 ml). The mixture was stirred for 10 minutes. The solvent was removed at 30° C. and passed through a column of XAD-8 resin. Eluting with ethanol gave the product as a solid (170 mg, 77%).

Analysis: Calculated for $C_{30}H_{38}O_7SNA_2 \cdot (H_2O)_{2\frac{1}{2}}$: C, 56.86; H, 6.84; S, 5.06. Found: C, 56.78; H, 6.82; S, 4.87.

EXAMPLE 58

Preparation of ethyl 2(E)-tridecenoate.

A mixture of undecaldehyde (13 g) and (carboethoxymethylene) triphenylphosphorane (29.3 g) in toluene (80 ml) was heated at 70° C. for 24 hours. The reaction mixture was cooled to room temperature, chromatographed directly on a column of silica gel (70–230 mesh, 300 g) eluting with hexa e (500 ml) and hexane-ethyl acetate (10:1) to afford a colorless oil (17 g) containing a few percent of the (Z)- isomer which was removed on Waters 500 PREP-LC using hexane-ether (10:0.3) as elutant to give the pure title compound as a colorless liquid (13.8 g, 75%). 1H NMR $(CDCl_3)\delta$: characteristic peaks: 4.15–4.25 (2H,q), 5.8(1H,d), 6.9–7.05 (1H, m).

EXAMPLE 59

Preparation of 1-hydroxy-2(E)-tridecene

A solution of the title compound of Example 58 (16.5 g) in THF (80 ml) was added to a cold suspension of $AlH_3 \cdot \frac{1}{3}$ ethyl ether (6.5 g) in THF (85 ml) and stirred at room temperature for 1 hour. The reaction mixture was cooled to 0° C. and saturated $NH_4Cl$ (300 ml) was added slowly and stirred at room temperature for 1 hour in the presence of ether (200 ml). The organic layer was separated and dried over $Na_2SO_4$ to give the title compound as a colorless liquid (13 g, 96%).

1HNMR $(CDCL_3)\delta$: characteristic peak: 4.10 (2H,d), 5.65–5.8 (2H, m).

EXAMPLE 60

Preparation of 1-bromo-2(E)-tridecene

A solution of the title compound of Example 59 (15.3 g) and $CBr_4$(25.6 g) in $CH_2Cl_2$ (140 ml) was cooled to 0° C. and to this solution was added dropwise a solution of DIPHOS (24.6 g) in $CH_2Cl_2$ (90 ml) and stirred for 10 minutes. The mixture was diluted with pentane (300 ml) and filtered. The filtrate was evaporated to give a mixture of oil and solid which was passed through a short column of silica gel (70–230 mesh) to give the title compound as a colorless oil (15.5 g, 77%).

1H NMR $(CDCl_3)\delta$: characteristic peaks 3.95 (2H, d), 5.6–5.85 (2H, m).

EXAMPLE 61

Preparation of 1-(diethyl phosphono)-2(E)-tridecene

Using the procedure as used for the preparation of 1-(diethyl phosphono)-2(E), 7(Z)-tridecadiene in Example 70 but replacing the 1-bromo-2(E), 7(Z)-tridecadiene by 1-bromo-2(E)-tridecene there was obtained the title compound (2.4 g, 100%).

1H NMR $(CDCl_3)\delta$: characteristic peaks: 2.4 and 2.65 (2H, 2d), 5.1(2H, quint.) 5.0–5.7(2H, m).

EXAMPLE 62

Preparation of ethyl 5(S)-trans-5,6-oxido-7(E), 9(E)eicosadienoate

Using the same procedure as described in Example 71 but replacing the 1-(diethyl phosphono)-2(E), 7(Z)-tridecadiene by 1-(diethyl phosphono)-2(E)tridecene there was obtained the title compound as an oil (380 mg, 20%). The sample was dissolved in hexane (2 ml), concentrated to about 1 ml and cooled overnight at 5° C. to afford a white solid (170 mg) which was shown by NMR to contain exclusively the 7(E) isomer, m.p. 32°–33° C. $a_D^{20}$ 31 29.8 (C=1.2, $CDCl_3$). The liquors (200 mg) correspond to 85% of 7(E) isomer.

EXAMPLE 63

Preparation of 1-(tetrahydropyran-2-yloxy)-5-undecyne

A solution of 1-(tetrahydropyran-2-yloxy)-5-hexyne (2.28 g) and triphenylmethane (5 mg) in THF (25 ml) was cooled to $-40°$ C. A solution of 1.6M in n-butyl lithium in hexane (8.3 ml) was then added. The solution was allowed to warm to 0° C. over 20 minutes and then cooled again to −40° C. Dry HMPA (hexamethylphosphorictriamide) (10 ml) was added followed by dropwise addition of iodopentane (1.64 ml). The mixture was warmed to room temperature over 6 hours, stirred overnight, and then poured into water (100 ml). The product was extracted with ether (3X 50 ml). The combined ether layers were washed with 5% aqueous sodium thiosulphate and water, dried over $Na_2SO_4$ and evaporated to give the title compound as an oil (3.0 g, 95%), which was used as such in Example 64.

EXAMPLE 64

Preparation of 1-(tetrahydropyran-2-yloxy)-5(Z) undecene

To a solution of nickelous acetate (1.0 g) in 95% ethanol (5 ml), flushed with nitrogen, was added a 0.5M solution of $NaBH_4$ in 95% ethanol (4 ml). Ethylene diamine (0.2 ml) was added. To this mixture, a solution of the title compound of Example 63 (1.0 g) in 95% ethanol (10 ml) was added, and the mixture was hydrogenated at 15 psi for 30 minutes The reaction mixture was filtered through a Celite bed and concentrated to dryness. The residue was extracted with hexane and chromatographed on a column of silica gel (70–230 mesh) eluting with hexane-ethyl acetate (10:1) to afford a colorless oil (850 mg, 85%).

$^1$H NMR ($CDC_3$)δ: characteristic peaks: 5.3–5.45 (2H, m).

EXAMPLE 65

Prearation of 1-hydroxy-5(Z)-undecene

To a solution of the title compound of Example 64 (18 g) in THF (20 ml) and methanol (10 ml) was added 1N HCl (10 ml) followed by stirring at room temperature for 20 hours. The mixture was diluted with $H_2O$ (100 ml) and extracted with ether. The combined organic layers were washed with brine and dried over $Na_2SO_4$ to give an oil which was purified on a column of silica gel, using hexane-ethyl acetate (10:1) as eluant to afford the title compound as a colorless oil (10.8 g, 90%).

$^1$H NMR ($CDCl_3$)δ: characteristic peaks: 1.95–2.15(4H, m), 3.65(2H, t), 5.3–5.45(2H, m).

EXAMPLE 66

Preparation of 5(Z)-undecenylic aldehyde

A mixture of the title compound of Example 65 (10.6 g), pyridinium chlorochromate (15.6 g) and Celite (50 g) in $CH_2Cl_2$ (100 ml) was stirred at room temperature for 4 hours, diluted with ether and filtered. The filtrate was concentrated and chromatographed on a column of silica gel eluting with ether-hexane (1:10) to give the title compound as a colorless oil (8.2 g, 77%).

$_1$H NMR ($CDCl_3$)δ: characteristic peaks: 1.65–1.8(2H, m), 1.95–2.15(4H, m), 2.45(2H, td), 5.25–5.5(2H, m).

EXAMPLE 67

Preparation of ethyl 2(E), 7(Z)-tridecadienoate

To a suspension of 99% NaH(1.25 g) in anhydrous DMF (40 ml) at 0° C. was added triethyl phosphonoacetate (11.2 g), under $N_2$. After the evolution of $N_2$ ceased, the mixture was stirred at room temperature for 15 minutes and cooled to 0° C. A solution of 5(Z)-undecenylic aldehyde (title compound of Example 66) (8.2 g) in anhydrous DMF (20 ml) was added dropwise and the mixture was stirred overnight at room temperature. The mixture was diluted with $H_2O$ (200 ml) and extracted with ethyl ether (3×150 ml). The extracts were washed with $H_2O$, and dried over $Na_2SO_4$. The filtrate was evaporated to give an oil (12 g) which was found to be a 20:1 mixture of E:Z isomers. The E isomer was purified on Waters 500 PREP-LC eluting with 2.5% ether in hexane to give the title compound as a colorless oil (7.8 g, 67%).

$^1$H NMR ($CDCl_3$)δ: characteristic peaks: 4.15–4.25 (2H, q), 5.25–5.45 (2H, m), 5.85 (1H, d), 6.9–7.05 (1H, m).

EXAMPLE 68

Preparation of 1-hydroxy 2(E), 7(Z)-tridecadiene

A solution of the title compound of Example 67 (7.73 g) in THF (40 ml) was added at 0° C. to a suspension of $AlH_3.\frac{1}{3}$ ethyl ether (2.3 g) in THF (30 ml) under $N_2$. The mixture was stirred at room temperature for 15 minutes, cooled to 0° C. and quenched with a cold saturated solution of ammonium chloride (50 ml). The product was extracted with ether (2X). The combined organic layers were washed with water, dried over $Na_2SO_4$ to give an oil which was purified on Waters 500 PREP-LC, using hexane ethyl acetate (10:1) as eluant, to afford the title compound as a colorless oil (4.7 g, 74%).

$^1$H NMR ($CDCl_3$)δ: characteristic peaks: 4.12 (2H, t), 5.2–5.35 (2H, m), 5.55–5.70 (2H, m).

EXAMPLE 69

Preparation of 1-bromo-2(E), 7(Z)-tridecadiene

To a solution of the title compound of Example 68(4.7 g) and $CBr_4$ (8 g) in $CH_2Cl_2$ (20 ml) at 0° C. under $N_2$ was added a solution of DIPHOS (7.9 g) in $CH_2Cl_2$ (60 ml). The reaction mixture was stirred at room temperature for 30 minutes, diluted with pentane (100 ml) and chromatographed on silica gel (70–230 mesh, 200 g) eluting with hexane and then with 1:9 ether-hexane to give the title compound as a colorless oil (4.61 g, 74%).

$^1$H NMR ($CDCl_3$)δ: characteristic peaks: 3.95 (2H, d), 5.2–5.35 (2H, m), 5.55–5.70 (2H, m).

EXAMPLE 70

Preparation of 1-(diethyl phosphono)-2(E), 7(Z)-tridecadiene.

To a suspension of 99% NaH (240 mg) in DMF (10 ml) at 0° C. in an atmosphere of argon was added diethyl-phosphite (1.3 ml) and the mixture was stirred at 0° C. for 1 hour and at room temperature for 4 hours. A solution of the title compound of Example 69 (2.07 g) in DMF (10 ml) was added at 0° C. and the mixture was stirred at room temperature for 15 hours. The mixture was diluted with $H_2O$ and extracted with ether (3X). The combined organic layers were washed with $H_2O$ and dried over $Na_2SO_4$ to give an oil which was chromatographed on silica gel (70–230 mesh), eluting with hexane-ethyl acetate (1:1) to give the title compound of a colorless oil (2.1 g, 84%). Analysis calculated for $C_{17}H_{33}O_3P$: C, 64.53: H, 10.51: P, 9.79. Found: C, 64.56; H, 10.30; P,9.94.

EXAMPLE 71

Preparation of ethyl 5(S)-trans-5,6-oxido-7(E), 9(E), 14(Z)- eicosatrienoate A solution of the title compound of Example 70 (1.38 g) in anhydrous THF (15 ml) was cooled to −30° C. under an atmosphere of argon. A solution of 0.665M KHMDS (Potassium hexamethyldisilazide) in toluene (6.54 ml) was then added dropwise and stirred at −30° C. for 45 minutes and then cooled to −78° C. A solution of ethyl 5(S)-trans-5,6-oxido-7-oxoheptanoate (870 mg) in anhydrous THF (7 ml) was added dropwise, stirred at −78° C. for 15 minutes and overnight at room temperature. The reaction mixture was poured into a mixture of 25% ammonium acetate in water (100 ml, pH7) and ethyl ether (150 ml) containing triethylamine (8 ml). The aqueous layer was extracted again with ether (100 ml, containing triethylamine (5 ml)). The organic layers were washed with brine and dried over $Na_2SO_4$ to give an oil (1.53 g). The oil was purified on a silica gel H (30 g) column which was previously deactivated with 20% triethylamine in hexane (1000 ml) and eluted with hexane-ether-triethylamine (10:1:0.2) to give the title compound as an oil (305 mg, 20%) which was shown by NMR to be 98% 7(E) isomer present in the oil.

$^1$H NMR (CDCl$_3$)δ: characteristic peaks: 2.80–2.90.(1H, m), 3.12 (1H, dd), 4.15 (2H, q), 5.2–5.45(3H, m), 5.65–5.8(1H, quintet), 6.0–6.1(1H, m), 6.3–6.45(1H, 4 peaks). $a_D^{20}$ -29.4 (c=1.6, CDCl$_3$).

What is claimed is:

1. Compounds having the formula:

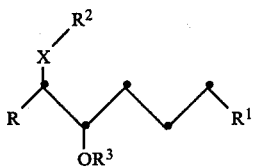

X is O, S, SO, SO$_2$;

R is selected from: —CH=CH—(C$_1$ to C$_{14}$ alkyl), —(CH=CH)$_2$—(C$_1$ to C$_{12}$ alkyl), —(CH=CH)$_3$—(C$_1$ to C$_{10}$ alkyl), —(CH=CH)$_3$—(CH$_2$—CH=CH)$_2$—(C$_1$ to C$_4$ alkyl), —(CH=CH)$_4$—(C$_1$ to C$_8$ alkyl), —CH$_2$—(CH=CH)$_4$—(C$_1$ to C$_7$ alkyl), —(CH=CH)$_3$—CH$_2$CH=CH—(CH$_2$)$_n$CH$_2$OH wherein n is 1 to 6, —(CH=CH)$_3$—CH$_2$CH=CH—(CH$_2$)$_n$COOR$^{11}$ wherein n is 1 to 6, —(CH=CH)$_3$—CH$_2$CH=CH—(C$_1$ to C$_7$ alkyl); —C≡C—(C$_1$ to C$_{14}$ alkyl), —CH=CH—C≡C—(C$_1$ to C$_{12}$ alkyl), —C≡C—(CH=CH)—(C$_1$ to C$_{12}$ alkyl), —C≡C—(CH=CH)$_2$—(C$_1$ to C$_{10}$ alkyl), and —C≡C—(CH=CH)$_2$—CH$_2$—CH=CH—(C$_1$ to C$_7$ alkyl);

R$^1$ is COOR$^{11}$;

R$^2$ is

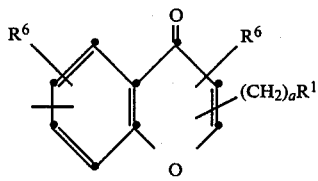

R$^3$ is H, lower alkyl, —(CH$_2$)$_a$COOR$^{11}$ or C$_1$ to C$_5$ acyl;

each R$^5$ is independently lower alkyl; CF$_3$; phenyl; or substituted phenyl, wherein the substituents are C$_1$ to C$_3$ alkyl, halogen, CN, CF$_3$, COOR$^8$ or C$_1$ to C$_3$ alkoxy;

R$^6$ is H, lower alkyl, OH, halogen, C$_1$ to C$_3$ perfluoroalkyl, CN, NO$_2$, C$_1$ to C$_5$ acyl, COOR$^8$, SO$_2$N(R$^8$)$_2$, N(R$^8$)$_2$, OR$^5$, SR$^5$, SOR$^5$, SO$_2$R$^5$, O-aryl, benzyl, benzyl substituted as defined for phenyl in R$^5$, or CH$_2$OH;

each R$^8$ is independently H or alkyl of 1 to 4 carbons which may be straight chain or branched;

R$^{11}$ is H, lower alkyl, phenyl-lower alkyl, lower alkoxy-lower alkyl, lower acyloxy-lower alkyl;

a is 0 to 4;

and pharmaceutically acceptable salt or lactone forms thereof.

2. Compound according to claim 1, having the Formula

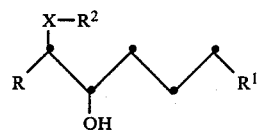

wherein: X is O or S,

3. The compound of claim 1:
 5,6-erythro-5-hydroxy-6-(2-carboxy-8-n-propyl-4-oxo-b rH-1-benzopyran-7-yl)thio-7,9-trans-11,14-cis-eicosatetraenoic acid;
 5,6-threo-5-hydroxy-6-(2-carboxy-8-n-propyl-4oxo-4H-1benzopyran-7-yl)thio-7,9-trans-11,14-cis-eicosatetraenoic acid;
 5,6-erythro-5-hydroxy-6-(2-carboxy-4-oxo-4H-1-benzopyran-7-yl)thio-7,9-trans-11,14-cis-eicosatetraenoic acid;
 5,6-threo-5-hydroxy-6-(2-carboxy-4-oxo-4H-1-benzopyran-7-yl)thio-7,9-trans-11,14-cis-eicosatetraenoic acid;
 5,6-erythro-5-hydroxy-6-(2-carboxy-4-oxo-4H-1-benzopyran-7-yl)oxo-7,9-trans-11,14-cis-eicosatetraenoic acid;
 5,6-erythro-5-hydroxy-6-(2-carboxy-8-n-propyl-4-oxo-4H-1-benzopyran-7-yl)thio-7,9,11-trans-14-cis-eicosatetraenoic acid;
 5,6-erythro-5-hydroxy-6-(2-carboxy-8-n-propyl-4-oxo-4H-1-benzopyran-7-yl)thio-7,9-trans-11-cis-eicosatrienoic acid;
 5(S)-hydroxy-6(R)-(2-carboxy-4-oxo-4H-1-benzopyran-7-yl)thio-7-cis-eicosenoic acid; or
 5(S)-hydroxy-6(R)-(2-carboxy-4-oxo-4H-1-benzopyran-7-yl)thio-7-trans-9-eicosadienoic acid.

4. A pharmaceutical composition useful in atagonizing leukotriene acting in mammals comprising an amount of a compound of claim 1 effective as a leukotriene antagonist and a pharmaceutically acceptable carrier.

5. A method of preventing the synthesis, the action or the release of SRS-A and the leukotrienes C$_4$, D$_4$, E$_4$ and B$_4$ in mammals, which comprises administering to said mammal an effective amount of a compound of claim 1.

6. The method of claim 5 wherein SRS-A, and leukotrienes C$_4$, D$_4$, and E$_4$ are affected.

7. The method of claim 5 wherein leukotriene B$_4$ is affected.

8. A method of inducing cytoprotection in mammals comprising administering to a mammal in need of such treatment a cytoprotective amount of a compound of claim 1.

* * * * *